(12) United States Patent
Nelson et al.

(10) Patent No.: US 10,704,042 B2
(45) Date of Patent: Jul. 7, 2020

(54) LIGATION-BASED RNA AMPLIFICATION

(71) Applicant: GE HEALTHCARE BIO-SCIENCES CORP., Marlborough, MA (US)

(72) Inventors: John R. Nelson, Clifton Park, NY (US); R. Scott Duthie, Schenectady, NY (US); Rohini Dhulipala, Kendall Park, NJ (US); Gregory A. Grossman, Halfmoon, NY (US); Anuradha Sekher, Belle Mead, NJ (US)

(73) Assignee: GE HEALTHCARE BIO-SCIENCES CORP., Marlborough, MA (US)

( * ) Notice: Subject to any disclaimer, the term of this patent is extended or adjusted under 35 U.S.C. 154(b) by 61 days.

(21) Appl. No.: 15/966,353

(22) Filed: Apr. 30, 2018

(65) Prior Publication Data

US 2018/0320172 A1 Nov. 8, 2018

Related U.S. Application Data

(63) Continuation of application No. 11/722,089, filed as application No. PCT/US2005/046800 on Dec. 22, 2005, now abandoned.

(60) Provisional application No. 60/685,661, filed on May 27, 2005, provisional application No. 60/638,937, filed on Dec. 23, 2004.

(51) Int. Cl.
*C12N 15/10* (2006.01)
*C12Q 1/6865* (2018.01)

(52) U.S. Cl.
CPC ....... *C12N 15/1096* (2013.01); *C12Q 1/6865* (2013.01)

(58) Field of Classification Search
None
See application file for complete search history.

(56) References Cited

U.S. PATENT DOCUMENTS

| 6,207,446 B1 * | 3/2001 | Szostak | C07K 14/82 435/287.2 |
| 7,727,722 B2 * | 6/2010 | Nelson | C07H 19/10 435/6.12 |
| 2002/0058270 A1 * | 5/2002 | Kurn | C12Q 1/6865 435/6.1 |

FOREIGN PATENT DOCUMENTS

EP 0369775 A2 * 5/1990 ........... C12Q 1/6865

OTHER PUBLICATIONS

Teter et al. Cell 1999; 97: 755-765. (Year: 1999).*

(Continued)

*Primary Examiner* — Angela M. Bertagna
(74) *Attorney, Agent, or Firm* — Eversheds Sutherland (US) LLP

(57) ABSTRACT

Methods of amplification, purification and detection of nucleic acid sequences especially RNA are described. One aspect of the method involves the hybridisation and subsequent ligation of a nucleic acid structure to the nucleic acid sequence desired to be manipulated. The methods require that the nucleic acid structure comprises a double stranded region and a single stranded region. The single stranded region is complementary to the RNA sequence of interest. The double stranded region may also contain additional functionalities which are then used subsequently in the method.

4 Claims, 8 Drawing Sheets

Specification includes a Sequence Listing.

(56) References Cited

OTHER PUBLICATIONS

Guatelli et al. Proceedings of the National Academy of Sciences, USA 1990; 87: 1874-1878 (Year: 1990).*
Sekiguchi et al. Biochemistry 1997; 36: 9073-9079 (Year: 1997).*
Sriskanda, V. and Shuman, S. Nucleic Acids Research 1998; 26: 3536-3541 (Year: 1998).*

* cited by examiner

Results of the volume density measurements, as plotted using Excel™ software (Microsoft Corporation).

A.

B.

A. Comparison between bioarrays using the same tissue with $r^2$ values.
B. Differential expression comparison between liver and kidney bioarrays.

A. Standard Curve.

B. DNA and RNA amounts before and after purification.

Results of the RiboGreen Assay for Example 10. A. Standard Curve. B. Chart of DNA and RNA amounts before and after purification.

HPLC analysis of exonuclease digested cRNA from Example 11. All results were normalized to 'C'.

LIGATION-BASED RNA AMPLIFICATION

CROSS-REFERENCE TO RELATED APPLICATIONS

This application is a continuation of U.S. application Ser. No. 11/722,089, filed Jun. 19, 2007, now abandoned, which is a filing under 35 U.S.C. § 371 and claims priority to international patent application number PCT/US2005/046800 filed Dec. 22, 2005, published on Jul. 6, 2006, as WO 2006/071776, which claims priority to U.S. provisional patent application Nos. 60/638,937 filed Dec. 23, 2004 and 60/685,661 filed May 27, 2005; the disclosures of which are incorporated herein by reference in their entireties.

FIELD OF THE INVENTION

The invention relates to a new method of amplification, purification and detection of nucleic acids.

BACKGROUND OF THE INVENTION

The ability to amplify the quantity of nucleic acid, especially specific nucleic acid sequences, in a sample is an important aspect of many molecular biology techniques and assays. Polymerase chain reaction (PCR), U.S. Pat. Nos. 4,683,195 and 4,683,202 has been widely used to achieve amplification of specific nucleic acid sequences. In this method a mixture of nucleic acid sequences is mixed with two short oligodeoxynucleotide primers which specify the specific sequences are to be amplified.

Many of the previous methods are related to amplification of DNA. However, there have been increasing attempts to amplify target RNA molecules. The amplification of RNA is important in areas such as expression analysis and viral detection. One technique involved in amplification of RNA is called RT-PCR. In this technique RNA molecules are copied into complementary DNA (cDNA) sequences by the action of reverse transcriptase. The cDNA is then amplified by DNA polymerase in conjunction with appropriate primers.

A separate methodology has been described by Van Gelder et al. U.S. Pat. Nos. 5,545,522, 5,716,785 and 5,891,636. Here RNA target molecules are reverse transcribed into cDNA by reverse transcriptase in conjunction with a primer which also combines a promoter sequence for T7 RNA polymerase. After double stranded cDNA has been produced, T7 RNA polymerase is added and multiple copies of complementary RNA (cRNA) are produced by transcription.

The method described by Van Gelder et al requires cDNA synthesis and is multi-step, requiring reverse transcriptase, RNAse, polymerase and ligase and also requires a purification step in the middle of the protocol. These additional steps add to the complexity and also cost of the synthesis of cRNA.

Recently it has been demonstrated that DNA dependent RNA polymerases (RNA polymerases) can replicate short fragments of RNA by transcription if the RNA molecule to be transcribed is attached to a double stranded DNA promoter. After transcription initiation by the RNA polymerase on the double stranded DNA region, transcription proceeds across the RNA-DNA junction and through the RNA region with no observable loss of speed or processivity. Additionally, the template RNA being transcribed can be single stranded RNA, double stranded RNA, or a DNA:RNA heteroduplex. The only requirement for this process being that the RNA polymerase must initiate transcription on a double stranded DNA segment (Arnaud-Barbe, et al. Nucleic Acid Research 26 3550-3554 (1998)).

DNA ligases catalyze the joining of DNA strands to one another, while RNA ligases catalyze the joining of RNA strands to one another. It is a common misconception that DNA ligase is very inefficient at ligation of DNA to RNA strands. It has been demonstrated, however, that DNA ligase catalyzes the efficient joining of 3'-OH-terminated RNA to 5'-phosphate-terminated DNA on a DNA scaffold (Arnaud-Barbe, et al, 1998). DNA ligase is much less effective at joining 3'-OH-terminated DNA to 5'-phosphate-terminated RNA (much like the nick present during Okazaki strand maturation prior to RNA primer removal) and is extremely weak at phosphodiester formation between two RNA strands (Sekiguchi and Shuman. Biochem 36: 9073-9079 (1997)).

Nath and Hurwitz J B C 249 3680-3688 (1974) described the covalent ligation of the 3'-OH of polyA to the 5'-phosphate of polydA provided a polydT sequence was present to provide hybridisation using either E-coli DNA ligase or T4 DNA ligase. Similar observations were reported by Fareed et al. (J. Biol. Chem. 246 925 (1971)).

SUMMARY OF THE INVENTION

At least one example embodiment of the present invention removes some of the steps mentioned in the previous amplification methods. Also the previous methods described to purify polyadenylated (poly(A)) mRNA do not attach the oligo(dT) sequence to RNA by a covalent bond, they only use base pairing (hydrogen bonding, which is not covalent) so buffer conditions need to be gentle. If ligation of sequence to end of RNA is used it results in very stable covalent attachment, allowing more stringent buffer conditions to be used.

The methods described involve the production of a nucleic acid structure and its subsequent use in the purification and amplification of nucleic acid. The methods require a DNA sequence that comprises a double stranded region and a single stranded region. The single stranded region is complementary to the RNA sequence of interest. The RNA sequence is then hybridized to the single stranded region of the DNA sequence and then the two sequences are ligated in a novel procedure to produce an RNA-DNA molecule.

The DNA sequence also contains an additional feature depending on the future use of the RNA-DNA molecule produced.

Embodiments also include methods whereby the 3' end of RNA is first ligated to a double stranded DNA oligonucleotide containing a promoter sequence. This double stranded DNA oligonucleotide contains a promoter for RNA polymerase within the double stranded region that is followed by a segment of single stranded DNA forming a 3' overhang. When the 3' overhang contains a string of thymidine residues, the single stranded portion of the double stranded DNA will hybridize to the 3' end of messenger RNA (mRNA) poly(A) tails. After the addition of ligase mRNA will have one strand of this double stranded DNA sequence ligated to the 3' end. When an RNA polymerase is added, these hybrid molecules will be efficiently transcribed to synthesize cRNA. As transcription reactions using RNA polymerase typically transcribe each template multiple times, this method allows for effective RNA amplification.

Another method similar to that described above involves the ligation of the DNA oligonucleotide to the RNA as described. However, the DNA oligonucleotide is either attached to a solid support or contains an affinity tag. This allows for very efficient covalent attachment and/or capture of RNA molecules, which can be used for any of a variety of purposes.

Yet another method utilizes the ligation and subsequent transcription to create complementary RNA containing a user-defined sequence at the 5' end of the cRNA. This sequence "tag" is placed between the RNA polymerase promoter and the 3' end of the ligated RNA molecule. The user-defined sequence can be used for purification or identification or other sequence specific manipulations of this cRNA. If this cRNA product is subsequently ligated and re-amplified according to the described method, the resulting doubly-amplified product will be "sense", with respect to the original sense template and this new product can have two separate user-defined sequences located at it's 5' ends. These sequences can be used for synthesis of cDNA, allowing for full-length synthesis and directional cloning. Those skilled in the art will understand that either with or without the user defined sequences, this double amplification method can provide a significant increase in RNA amount, allowing for analysis of samples previously too small for consideration.

BRIEF DESCRIPTION OF THE FIGURES

FIGS. 5A-5F show hybridisation results obtained from various on tissues on arrays, in which FIG. 5A shows Kidney Total RNA without ligase added to the ligation (T1); FIG. 5B shows Liver Total RNA without ligase added to the ligation (T2); FIG. 5C shows Kidney Total RNA plus ligase without SDS added to the reaction (T3); FIG. 5D shows Kidney Total RNA plus ligase with SDS added to the reaction (T5); and FIG. 5F shows Liver Total RNA plus ligase with SDS added to the reaction (T5).

FIGS. 6A and 6B show results from FIGS. 5A-5F in chart form, in which FIG. 6A shows the comparison between bioarrays using the same tissue with $r^2$ values, and FIG. 6B shows the differential expression comparison between liver and kidney bioarrays.

Figure 1:
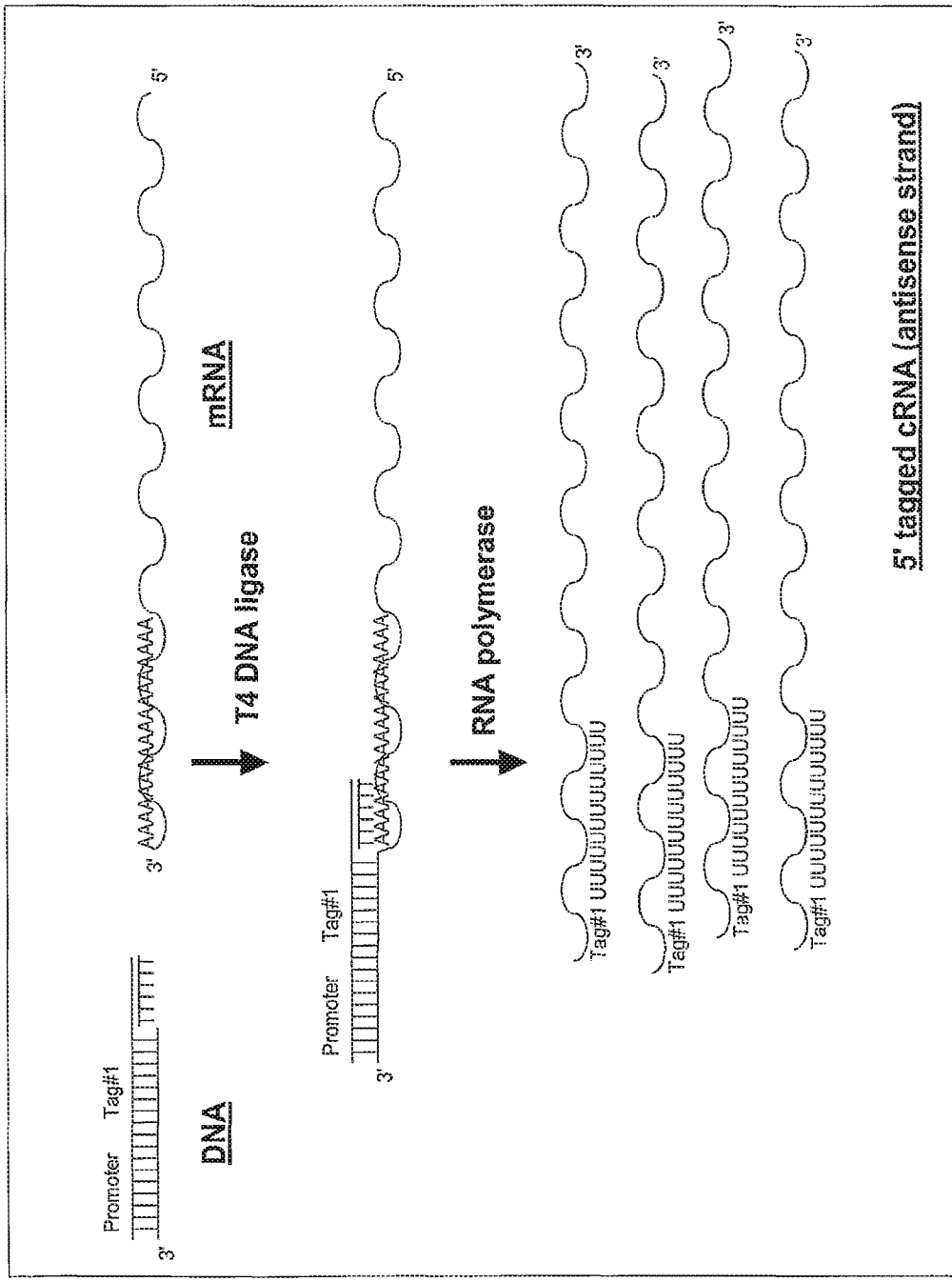
FIG. 1 is a schematic representation of the initial ligation and subsequent transcription reactions. The mRNA shown has a representative poly(A) tail (SEQ ID NO:18). The 5' tagged cRNA has a poly(U) stretch represented by SEQ ID NO:19.

DETAILED DESCRIPTION OF THE INVENTION a) Outline

The methods described involve the novel production of a nucleic acid structure and its subsequent use in purification and amplification of nucleic acid. The methods require a DNA sequence that comprises both a double stranded region and a single stranded region. Note that this conformation may be formed by mixing two DNA oligos together or by using on oligo capable of forming a hairpin loop. The single stranded region is complementary to the RNA sequence of interest and may contain either: 1) a poly(dT) sequence, e.g., 5'-d[ . . . (T)x]-3' where X may be any whole number and ' . . . ' represents one strand of the preceding double stranded region, or 2) a poly(dT) sequence with variable nucleotide sequences at the 3' end, e.g., 5'-d[ . . . TTT(V)x (N)x]-3' where V may be A, C, or G, N may be any of all four nucleotides, X may be any whole number and ' . . . ' represents one strand of the preceding double stranded region. RNA is then hybridized to the single stranded region of the DNA sequence and the two sequences ligated in a novel procedure to produce an RNA-DNA molecule. One skilled in the art will recognize that the poly(dT) portion may be eliminated so that the composition of the single stranded would be 5'-d[ . . . (V)x(N)x]-3', d[ . . . (V)x]-3', or d[ . . . (N)x]-3'.

b) Nucleic Acid Consideration

The methods described have particular use in the amplification and purification of RNA. The RNA can come from a variety of sources but the methods are particularly suitable for eukaryotic mRNA containing polyA tails. For example the RNA can come from human or other animal sources and could be part of studies comparing RNA samples between healthy and disease/infected populations or between treated and control samples and could also include RNA for evaluation from individuals to aid in diagnostic procedures, disease vs healthy, cancer vs non, treated vs non for experimental, drug screening, infectious agent screening. The RNA is usually a mixture of different RNA sequences from the sample and comprises RNA sequences with the four naturally occurring bases A,C,G and U. Other unusual or modified bases may also be present.

The generation of multiple copies of RNA, particularly labeled RNA, is important for a number of applications. These include situations where samples are limited such as fetal origin, aged persons, single cell or limited cell analysis, patient biopsy, high throughput laboratories, samples which are dilute, such as rare event screening such as cells in mixed samples such as cancer cells in blood during metastatic or pre-metastatic cancer, environmental samples (biowarf are detection, water purity, food testing).

c) Initial Hybridization and Ligation

The RNA sample is mixed with a nucleic acid sequence that comprises or nucleic acid sequences that comprise a double stranded region and a single stranded region. The single stranded region of the nucleic acid sequence hybridizes to the RNA. Ligation of one 5' end of the double stranded region of the nucleic acid to the 3' end of RNA is achieved by enzymatic means. The nucleic acid sequence used may be DNA, RNA, a combination of DNA and RNA or nucleic acid analogues such as PNA. The nucleic acid sequence may comprise two separate strands of different length or may be a single strand which contains a hairpin structure allowing for the formation of a double stranded region and a single stranded region.

For convenience a detailed description is provided where the nucleic acid sequence comprises DNA. As shown in FIG. 1, the first step of the one example embodiment of the present invention is to ligate a DNA sequence to the 3'end of mRNA sequence. This DNA sequence comprises a double strand region and a single stranded region. The single stranded region is used to hybridize the 3' end of the mRNA and position the double stranded region adjacent to the RNA sequence. As shown, the single stranded DNA (portion/region) may be composed of several T residues (poly dT) which then hybridize to the poly A tail of the mRNA. The poly dT sequence can be 1 to 100 long, more preferably 3 to 25 long.

It has been found that the ligation of the DNA sequence to the 3' end of the mRNA can be achieved by the use of many different DNA or RNA ligase enzymes. T4 DNA ligase has been shown to be particularly suitable. The recessed 5' end of the DNA requires a phosphate group for successful ligation.

Depending on the intended use for the RNA-DNA molecule which is later produced, the double stranded DNA portion/region of the molecule comprises at least one of the following features. In a first instance an affinity tag may be present which allows the separation and purification of the RNA-DNA molecule and hence provides a simple method of RNA purification. Examples of affinity tags include biotin which can be bound to avidin or streptavidin coated supports or other tag/binding partners e.g. His tags or antibodies and other systems well known to those skilled in the art. The affinity tag may be present at the 3' end of the ligated DNA.

Secondly a promoter sequence for RNA polymerase activity can be incorporated into the double stranded DNA sequence. These are well known and the most preferable sequence is the one for T7 RNA polymerase although sequences for SP6 or T3 RNA can be used. Indeed any DNA dependent RNA polymerase that requires a double stranded promoter sequence for the initiation of RNA synthesis recognition would function in this system. The RNA polymerase promoter is ideally located 1-40 base pairs from the 5' end of the oligonucleotide.

Additionally, a tag region (depicted as Tag #1 in FIG. 1) can be introduced into the double stranded DNA region downstream from the site of transcription, prior to the RNA-DNA function. This region which allows for the subsequent manipulation of the nucleic acid structure that has been produced by ligation or ligation followed by amplification. One example of a Tag region is a nucleotide sequence for restriction enzyme cleavage. Other examples of tag regions include nucleotide sequences for binding of other protein molecules.

It is also possible that the hybridisation/annealing of the double stranded DNA sequence to the RNA is stimulated by a double stranded DNA sequence located immediately adjacent to the subsequent ligation point which contains a nucleotide sequence which is involved in co-operative binding of nucleic acid sequences.

Further examples of a Tag could be dyes or radioactivity.

d) Purification

If a suitable affinity tag has been included in the nucleic acid sequence, preferably at the 3' end of the nucleic acid sequence, which is subsequently ligated to the RNA sequence then purification of the ligated RNA-nucleic acid molecule can be achieved. In some embodiments the nucleic acid sequence comprises DNA, preferably double stranded DNA. The affinity tag is preferably included in the double stranded DNA region of the DNA sequence so that possible interference of hybridization to the RNA is minimized.

Because the RNA is ligated to the nucleic acid sequence and hence indirectly to the affinity tag then much more stringent purification conditions can be used compared with other methods which rely on base pairing (hydrogen bonding) of the RNA. This is schematically represented in the first part of FIG. 1. If the only intended use is in purification the double strand DNA region need not contain an RNA polymerase promoter region. The affinity tag can include examples such as biotin, digoxigen, fluorescein, His Tags and many other well known in the art.

e) Amplification

As shown in FIG. 1 the ligated DNA-RNA molecule can serve as a template for RNA synthesis using the promoter sequence contained in the ligated double stranded DNA molecule. Different RNA polymerases may be used but T7 RNA polymerase is preferred. Transcription of the ligated DNA-RNA molecules produces multiple copies of RNA complimentary to the original starting mRNA sequence i.e., it is an antisense strand cRNA. A tag region [shown as Tag #1] can also have been introduced into the 5' region of the cRNA.

f) Subsequent Hybridization and Ligation

Figure 2:
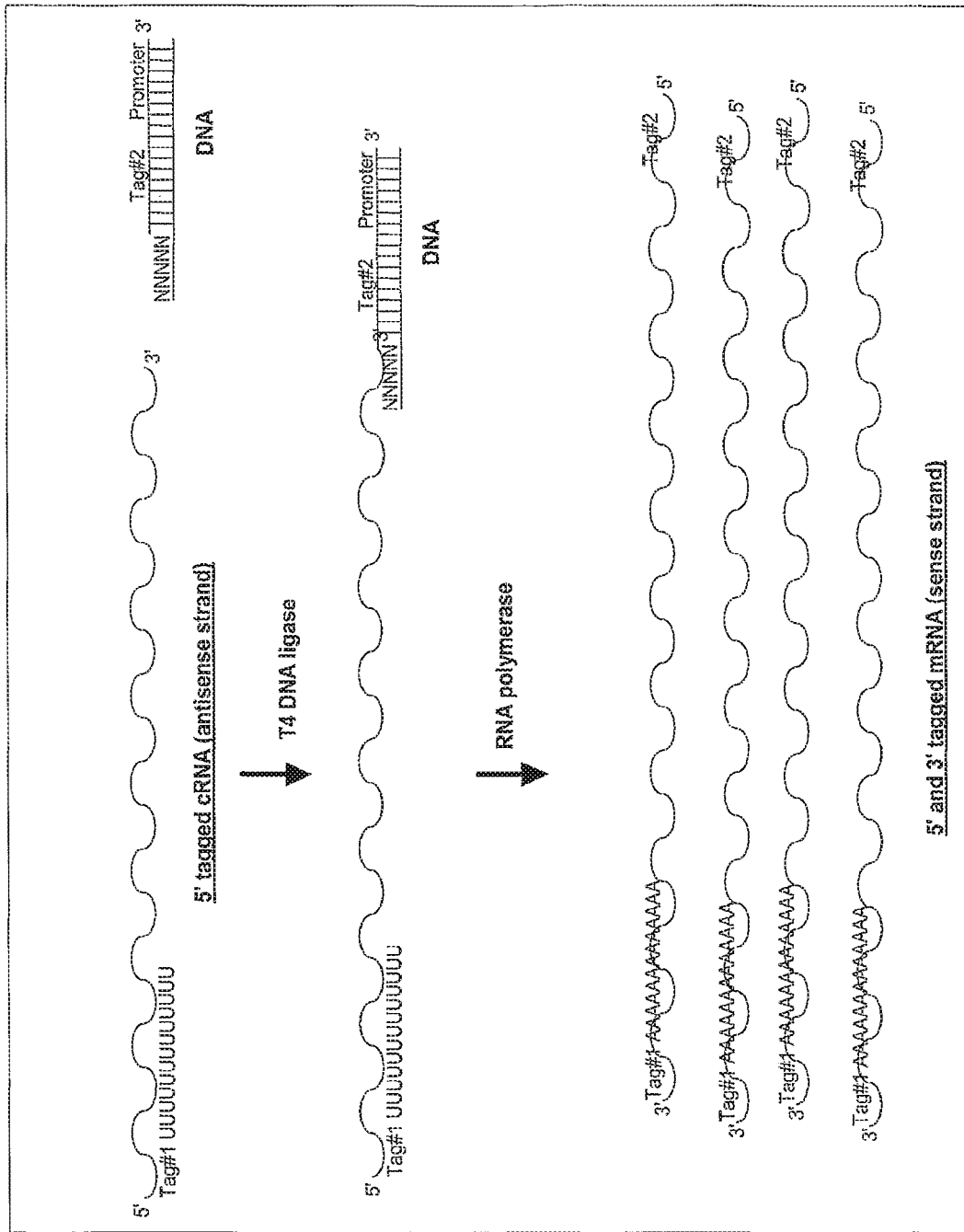
FIG. 2 is a schematic representation of further ligation and transcription reactions. Here, the 5' tagged cRNA has a poly(U) stretch represented by SEQ ID NO:19. The 5' and 3' tagged mRNA has a corresponding poly(A) stretch (SEQ ID NO:20).

As shown in FIG. 2 the 5' tagged cRNA [antisense strand] produced by the reaction scheme of FIG. 1 can now be hybridized and ligated to a further DNA sequence. This DNA sequence is of generally the same DNA structure as shown in FIG. 1 but as shown in FIG. 2 the single stranded region is not poly dT but is composed of a random sequence of bases which acts to hybridize to 3' end of the antisense strand. In addition the single stranded DNA region may also have a specific known sequence so that a specific RNA is amplified.

The double stranded region may contain a different Tag region designated Tag 2 but the Tag may be the same as Tag 1 used previously. It is of course possible to the use the method for amplification without the use of any Tags. The promoter sequence may be the same as the sequence used previously and is preferably the same but however a different promoter sequence may be used. After hybridization the mixture is ligated with T4 DNA ligase to produce a ligated cRNA-DNA hybrid.

The ligated cRNA-DNA can then be used to transcribe multiple copies of RNA using the appropriate RNA polymerase. T7 RNA polymerase is suitable for this step but SP6 RNA polymerase, T3 RNA polymerase and *E. coli* RNA polymerase may also be used. The RNA produced in this reaction is in the same sense as the starting RNA shown in figure but is present in multiple copies and can have two different Tag regions present as shown in FIG. 2.

g) cDNA Synthesis

Figure 3:
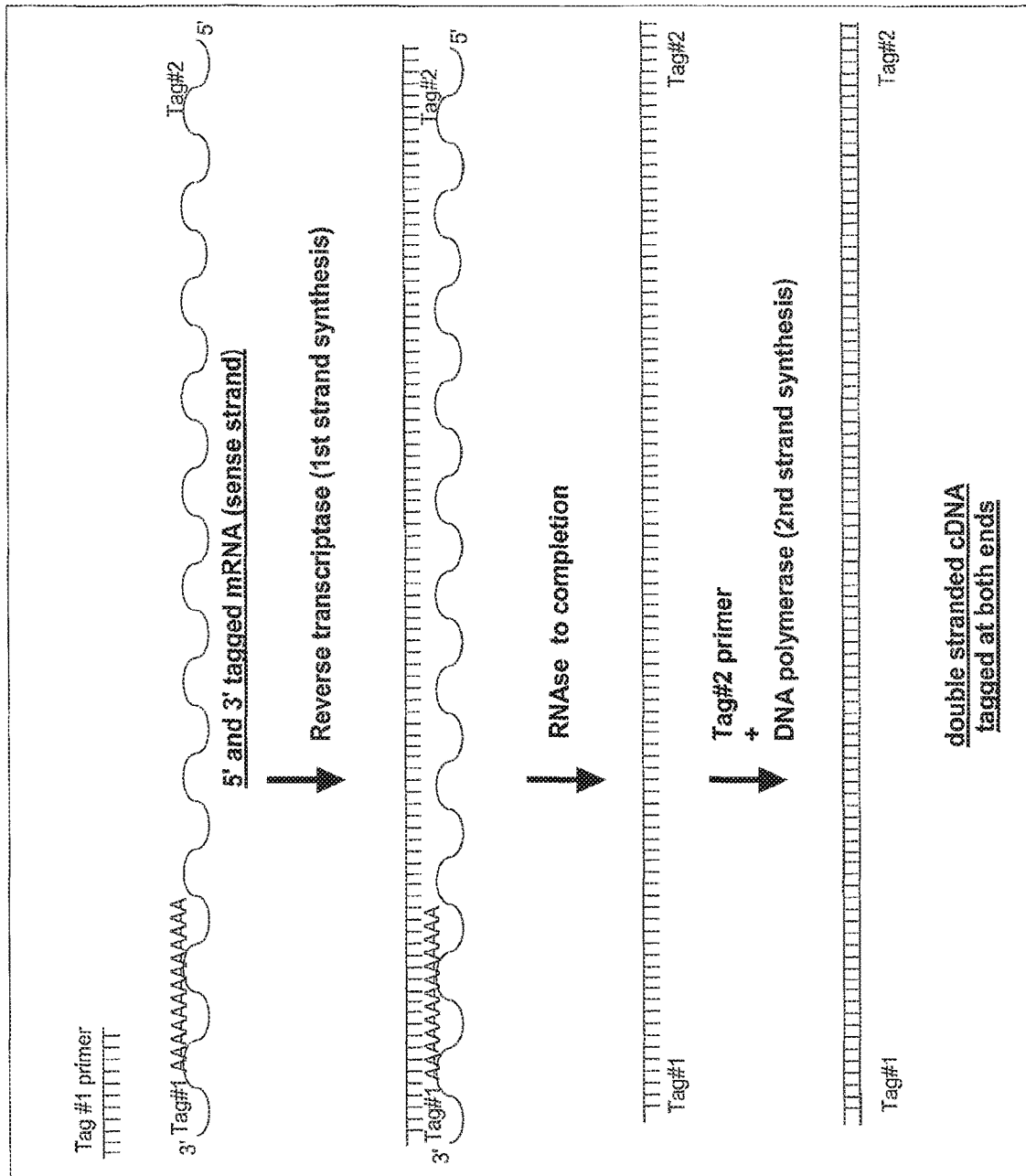
FIG. 3 is a schematic representation of the methods to produce cDNA. Note the 5' and 3' tagged mRNA has a corresponding poly(A) stretch (SEQ ID NO:20).

The RNA produced as described in FIG. 2 or for that matter any of the figures, can be used to produce cDNA as shown in FIG. 3. The RNA is hybridized with a single stranded DNA primer containing the compliment to the Tag #1 sequence. The RNA-DNA hybrid is then used to synthesize first strand cDNA using reverse transcriptase and dNTPs. Once first strand cDNA synthesis is complete, RNAse is used to remove the RNA of the heteroduplex. Second strand synthesis is done using Tag #2 primer DNA polymerase and dNTPs which produces full length cDNA which has the a Tag sequence at both ends. The cDNA has multiple uses including protein expression, RNA splice site analysis and gene discovery.

h) Removal of Nucleic Acid Sequences

For many applications it may be desirable to remove unused nucleic acid sequences. For example, DNA sequences which did not ligate to the RNA can be removed by treating the reaction products at the appropriate stage with a suitable exonuclease such as lambda exonuclease or T7 gene 6 exonuclease.

i) Nucleotide Considerations

For many of the applications described the standard nucleotides eg rNTPs (UTP, ATP, GTP and CTP) or dNTPs (UP, dATP, dGTP and dCTP) may be used. However, it is possible for some applications that it will be desirable to add nucleotide analogues such as methylated nucleotides or nucleotides such as rNTPaS or dNTPaS. A mixture of standard nucleotides and nucleotide analogues may be appropriate.

j) Further Considerations

The skilled person will realize that further variations to components and of the method are possible.

The DNA sequence comprising a double stranded and single stranded regions may be further modified to contain nucleotide analogues which are resistant to exonuclease degradation. In this circumstance, it is preferred to have the modified nucleotide analogues in the DNA strand which does not ligate to the target RNA.

In some methods it is also possible to add additional complementary top strand oligonucleotides either before or after exonuclease digestion.

It is also possible to add additional oligonucleotides to the transcription reactions. The additional oligonucleotides may be polyA or polydA although other sequences are possible.

The ligated DNA-cRNA molecule produced by the methods described may also be treated with reverse transcriptase prior to transcription.

The RNA produced in any of the methods described (either cRNA or amplified target RNA) can be used for a variety of purposes including the use of immobilised nucleic acid, especially in microarray format, for the purpose of RNA analysis.

The input RNA can be treated with an RNase in the presence of an oligonucleotide such the RNA is nicked at a specific location defined by the oligonucleotide. The oligonucleotide may contain methylated nucleotides in addition to standard nucleotides. The oligonucleotide may contain a randomized sequence of bases or a specific defined sequence.

This method is disclosed in example 11. The method comprises hybridizing an oligodeoxyribonucleotide which contains natural and modified nucleotides to an RNA sequence, contacting the resulting RNA-DNA hybrid with an agent that specifically nicks only the RNA strand and ligating a DNA sequence to the trimmed RNA 3' tail. The oligodeoxynucleotide should ideally be greater than eight nucleotides long and the nucleotides which are modified can be modified by methylation of 2'-OH group. The agent used to nick only the RNA strand is preferably RNAse H. The nicked RNA produced by this embodiment can then be used in the previous embodiments to produce amplified quantities of the RNA which can be labelled by the methods outlined previously as appropriate.

EXAMPLES

The present examples are provided for illustrative purposes only, and should not be construed as limiting the scope of the present invention as defined by the appended claims. All references given below and elsewhere in the present specification are hereby included herein by reference.

Materials

Water

All water used in these examples, including water used to prepare electrophoresis buffer, had been treated with diethyl pyrocarbonate (DEPC) and autoclaved to remove any contaminating RNA nucleases. The water used in preparation of ligation or transcription reactions was DEPC-treated and obtained from Ambion.

PT7IVS5 (Qiagen Operon)

(SEQ ID NO: 1)
Oligo 5'-d[GTAATACGACTCACTATA_GGGAG_(T̲)_24_]-3'

The deoxyribooligonucleotide (oligo) is composed of three parts.
1) The promoter sequence for T7 RNA polymerase is indicated in bold (Lopez, et al. J. Mol. Biol. 269: 41-51 (1997).
2) A five base intervening sequence (IVS), or that sequence complementary to the start site of transcription to where the poly(dT) sequence starts, is indicated in italics.
3) A 24 base poly(dT) sequence, or the sequence used to "capture" the mRNA 3' poly(rA) tail, is underlined.

cPT7IVS5 (Qiagen Operon)

(SEQ ID NO: 2)
Oligo
5'-Phosphate-d[_AAAACTCC_C̲TATAGTGAGTCGTATTAC]-3'

The oligo is composed of four parts and is the template for RNA synthesis.
1) The 5' phosphate group participates in covalent bond formation with the 3' hydroxyl group of mRNA.
2) Four dA residues in a row in italics promote complementary binding of the 3' poly(rA) tail of mRNA.
3) The first base transcribed by the RNA polymerase is indicated by the underlined C. Synthesis would proceed towards the 5' end of the cPT7IVS5 oligo into the attached mRNA sequence.
4) Sequence complementary to the promoter sequence is indicated in bold.

PT7IVS15 (Qiagen Operon)

(SEQ ID NO: 3)
Oligo
5'-d[AAATTAATACGACTCATATA_GGGAGACCACAACGG_(T̲)_24_]-3'

The oligo is composed of three parts.
1) The promoter sequence for T7 RNA polymerase is indicated in bold.
2) A 15 base IVS, or that sequence complementary to the start site of transcription to where the poly(dT) sequence starts, is italicized.
3) A 24 base poly(dT) sequence, or the sequence used to "capture" the mRNA 3' poly(rA) tail, is underlined.

cPT7IVS15 (Qiagen Operon)

(SEQ ID NO: 4)
Oligo 5'-Phosphate-
d[_AAAACCGTTGTGGTCTCC_C̲TATAGTGAGTCGTATTAATTT]-3'

The oligo is composed of four parts and is the template for RNA synthesis.
1) The 5' phosphate group participates in covalent bond formation with the 3' hydroxyl group of mRNA.
2) Four dA residues in a row in italics promote complementary binding of the 3' poly(rA) tail of mRNA.
3) The first base transcribed by the RNA polymerase is indicated by the underlined C. Synthesis would proceed towards the 5' end of the cPT7IVS5 oligo through the IVS into the attached mRNA sequence.
4) Sequence complementary to the promoter sequence is indicated in bold.

RNA₃₅ (Dharmacon)

(SEQ ID NO: 5)
Oligo 5'-r[UGUUG(U)₃₀]-3'

A synthetic RNA designed to test ligation and transcription reactions. The 3'-hydroxyl of this molecule becomes joined to the 5'-phosphate group of the cPT7 oligos (IVS5 or IVS15) through the actions of a ligase enzyme.
RNA₆₅ (Dharmacon)

(SEQ ID NO: 6)
Oligo 5'-r[UACAACGUCGUGACUGGGAAAAC(A)₄₂]-3'

A synthetic RNA designed to test ligation and transcription reactions. The 3'-hydroxyl of this molecule becomes joined to the 5'-phosphate group of the cPT7 oligos (IVS5 or IVS15) through the actions of a ligase enzyme.
PT3w/T24 (Qiagen Operon)

(SEQ ID NO: 7)
Oligo
5'-d[AAATAATTAACCCTCACTAAAGGGAGACCACAACGG(T)₂₄]-3'

The oligo is composed of three parts.
1) The promoter sequence for T3 RNA polymerase is indicated in bold (Ling M-L, et al. Nucl. Acids Res 17: 1605-1618 (1989)).
2) A 15 base IVS, or that sequence complementary to the start site of transcription to where the poly(dT) sequence starts, is italicized.
3) A 24 base poly(dT) sequence, or the sequence used to "capture" the mRNA 3' poly(rA) tail, is underlined.
cPT3 (Qiagen Operon)

(SEQ ID NO: 8)
Oligo 5'-Phosphate-
d[AAAACCGTTGTGGTCTCCCTTTAGTGAGGGTTAATTATTT]-3'

The oligo is composed of four parts and is the template for RNA synthesis.
1) The 5' phosphate group participates in covalent bond formation with the 3' hydroxyl group of mRNA.
2) Four dA residues in a row in italics promote complementary binding of the 3' poly(rA) tail of mRNA.
3) The first base transcribed by the RNA polymerase is indicated by the underlined C. Synthesis would proceed towards the 5' end of the cPT7IVS5 oligo through the IVS into the attached mRNA sequence.
4) Sequence complementary to the promoter sequence is indicated in bold.
Poly dA₂₀ (Integrated DNA Technologies, INC.; IDT)

(SEQ ID NO: 9)
Oligo 5'-d[AAAAAAAAAAAAAAAAAAAA]-3'

Biotin-cPT7IVS15 (Qiagen Operon)

(SEQ ID NO: 10)
Oligo 5'-Phosphate-
d[AAAACCGTTGTGGTCTCCCTATAGTGAGTCGTATTAATTT]-
Biotin-3'

The oligo is composed of five parts and is the template for RNA synthesis.
1) The 5' phosphate group participates in covalent bond formation with the 3' hydroxyl group of mRNA.
2) Four dA residues in a row in italics promote complementary binding of the 3' poly(rA) tail of mRNA.
3) The first base transcribed by the RNA polymerase is indicated by the underlined C. Synthesis would proceed towards the 5' end of the Biotin-cPT7IVS15 oligo through the IVS into the attached mRNA sequence.
4) Sequence complementary to the promoter sequence is indicated in bold.
5) A biotin group has been attached to the 5 position on the base of the ultimate 3' 'T' residue.
OHThioPT7IVS25 (Qiagen Operon)

(SEQ ID NO: 11)
5'-d[A*A*AAATAATACGACTCACTATAGGGAGTAATAGGACTCAC
TATAGGG(T₉)]-3'

The oligo is composed of four parts.
1) Two overhanging 'A' residues linked by phosphorothioate bonds (*).
2) The promoter sequence for T7 RNA polymerase is indicated in bold.
3) A 25 base IVS, or that sequence complementary to the start site of transcription to where the poly(dT) sequence starts, is italicized.
4) A 24 base poly(dT) sequence, or the sequence used to "capture" the mRNA 3' poly(rA) tail, is underlined.
HT-III 10c (SEQ ID NO: 12)
Oligo 5'-mUmUmUdTdTdTdTdTdVmN-3'

The oligo is composed of four parts.
1) Three 2'-O-methyl uridine monophosphate residues and five deoxythmidine monophosphate residues target the oligo to the polyA tail of mRNA.
2) dV and mN are degenerate bases, dV being only 'A', 'C', or 'G' and mN being all four bases with a 2'-O-methylation, that anchor the oligo to the last two bases of the mRNA message just 5' to the poly(A) tail.
3) The methylated residues prevent RNase H from nicking the mRNA outside the dT region.
4) Five dT residues allow RNase H to bind and target nicking of the mRNA within this region.
HT-III 10d (SEQ ID NO: 13)
Oligo 5'-mUmUmUdTdTdTdTdTdVdN-3'

The oligo is composed of four parts.
1) Three 2'-O-methyl uridine monophosphate residues and five deoxythmidine monophosphate residues target the oligo to the polyA tail of mRNA.
2) dV and N are degenerate bases, dV being only 'A', 'C', or 'G' and N being all four bases, that anchor the oligo to the last two bases of the mRNA message just 5' to the polyA tail.
3) The 2'-O-methyl residues prevent RNase H from nicking the mRNA outside the dT region.

4) Five dT residues allow RNase H to bind and target nicking of the mRNA within this region.

HT-III 10g (SEQ ID NO: 14)
Oligo 5'-mUmUmUmUdTdTdTdTdVmN-3'

The oligo is composed of four parts.
1) Four 2'-O-methyl uridine monophosphate residues and four deoxythmidine monophosphate residues target the oligo to the polyA tail of mRNA.
2) dV and mN are degenerate bases, dV being only 'A', 'C', or 'G' and mN being all four bases with a 2'-O-methylation, that anchor the oligo to the last two bases of the mRNA message just 5' to the polyA tail.
3) The 2'-O-methyl residues prevent RNase H from nicking the mRNA outside the dT region.
4) Four dT residues allow RNase H to bind and target nicking of the mRNA within this region.

HT-III B5

(SEQ ID NO: 15)
Oligo 5'-
d[CGCAAATTAATACGACTCACTATAGGGAGACCACAACGGTTTVN]-3'

The oligo is composed of four parts.
1) The promoter sequence for T7 RNA polymerase is indicated in bold.
2) A 15 base IVS, or that sequence complementary to the start site of transcription to where the poly(dT) sequence starts, is italicized.
3) A 3 base poly(dT) sequence, or part of the sequence used to "capture" the mRNA 3' poly(rA) tail, is underlined.
4) V and N are degenerate bases, V being only 'A', 'C', or 'G' and N being all four bases, that anchor the oligo to the last two bases of the mRNA message just 5' to the polyA tail.

cpT7'-IR$_{15}$-(NoA)5'P (SEQ ID NO: 16)
Oligo 5'-Phosphate-d[CCGTTGTGGTCTCCCTATAGTGAGTCGTATTAATTTGCG]-3'

The oligo is composed of four parts and is the template for RNA synthesis.

1) The 5' phosphate group participates in covalent bond formation with the 3' hydroxyl group of mRNA.
2) The first base transcribed by the RNA polymerase is indicated by the underlined C. Synthesis would proceed towards the 5' end of the cPT7IVS5 oligo through the IVS into the attached mRNA sequence.
3) Sequence complementary to the promoter sequence is indicated in bold.
4) A 15 base IVS is indicated by italics.

HT-111 10f (SEQ ID NO: 17)
Oligo 5'-mUmUmUmUmUdTdTdTdVmN

The oligo is composed of four parts.
1) Five 2'-O-methyl uridine monophosphate residues and four deoxythmidine monophosphate residues target the oligo to the polyA tail of mRNA.
2) dV and mN are degenerate bases, dV being only 'A', 'C', or 'G' and mN being all four bases with a 2'-O-methylation, that anchor the oligo to the last two bases of the mRNA message just 5' to the polyA tail.
3) The 2'-O-methyl residues prevent RNase H from nicking the mRNA outside the dT region.
4) Three dT residues allow RNase H to bind and target nicking of the mRNA within this region.

Ligase

Any enzyme capable of forming intra- or inter-molecular covalent bonds between a 5'-phosphate group on a nucleic acid and a 3'-hydroxyl group on a nucleic acid. The examples include T4 DNA Ligase, T4 RNA Ligase and *E. coli* DNA Ligase.

Example 1: Ligation of Double Stranded DNA to Synthetic RNA

All ligation reaction components except *E. coli* DNA Ligase (New England Biolabs; 10 units/μL) were mixed as indicated in Table 1. The reactions were heated at 60° C. for five minutes and allowed to cool to room temperature. *E. coli* DNA Ligase was added to the appropriate tubes and the reactions incubated at 30° C. for two hours. Each reaction was stopped by the addition of 1 μL RNase-free 0.5 M EDTA (US Biochemicals, Inc.).

TABLE 1

Ligation reaction formulations for Example 1.

| Component | ID | | | | | | |
|---|---|---|---|---|---|---|---|
| | 1 | 2 | 3 | 4 | 5 | 6 | 7 |
| Water (Ambion) | 16 μl | 15 μl | 16 μl | 15 μl | 14 μl | 13 μl | 15 μl |
| 10X *E. coli* Ligase Buffer | 2 μl | 2 μl | 2 μl | 2 μl | 2 μl | 2 μl | 2 μl |
| SUPERASE.IN ™(Ambion 20 Units/μl) | 1 μl | 1 μl | 1 μl | 1 μl | 1 μl | 1 μl | 1 μl |
| PT7IVS15 (15 pmol/μl) | 1 μl | 1 μl | | | | | 1 μl |
| cPT7IVS15 (15 pmol/μl) | | | 1 μl | 1 μl | | | 1 μl |
| RNA$_{35}$ (16 pmol/μl) | | | | | 3 μl | 3 μl | |
| *E. coli* Ligase | | 1 μl | | 1 μl | | 1 μl | |
| Total Volume | 20 μl | 20 μl | 20 μl | 20 μl | 20 μl | 20 μl | 20 μl |

TABLE 1-continued

Ligation reaction formulations for Example 1.

| Component | ID 8 | 9 | 10 | 11 | 12 |
|---|---|---|---|---|---|
| Water | 14 μl | 12 μl | 11 μl | 15 μl | 14 μl |
| 10X E. coli Ligase Buffer | 2 μl | 2 μl | 2 μl | | |
| SUPERASE.IN ™ | 1 μl | 1 μl | 1 μl | 1 μl | 1 μl |
| PT7IVS15 (15 pmol/μl) | 1 μl | 1 μl | 1 μl | 1 μl | 1 μl |
| cPT7IVS15 (15 pmol/μl) | 1 μl | 1 μl | 1 μl | | |
| RNA$_{35}$ (16 pmol/μl) | | 3 μl | 3 μl | 3 μl | 3 μl |
| E. coli Ligase | 1 μl | | 1 μl | | 1 μl |
| Total Volume | 20 μl | 20 μl | 20 μl | 20 μl | 20 μl |

Five microliter samples of every reaction were mixed with 5 μl of Gel Loading Buffer II (Ambion) and heat denatured at 95° C. for two minutes. The entire amount of each sample was loaded into separate wells of 15% acrylamide, 7M urea TBE gels (Invitrogen) and subjected to electrophoresis at room temperature following the manufacturer's recommendations. Samples were loaded in numerical order from left to right, respectively, with DNA molecular weight makers interspersed. Electrophoresis was stopped when the bromophenol blue (BPB) loading dye was at the bottom of the gel. Each gel was stained by soaking in a 1:200 dilution of SYBR™ Gold Dye (Molecular Probes) in water for 10 minutes. After staining the gels were rinsed with distilled water and the DNA bands visualized by scanning in a TYPHOON™ 8600 Variable Mode Imager (TYPHOON™; GE Healthcare Bio-Sciences).

The gels were scanned using the green (532) laser and fluorescein 526 SP emission filter.

The DNA molecular weight markers are a mixture of 100 Base-Pair Ladder (0.5 μg), Homo-Oligomeric pd(A)40-60 (1.25×10$^{-3}$ A260 Units) and Oligo Sizing Markers (8-32 bases; 0.75 μl; all from GE Healthcare Bio-sciences). The results show that the three separate nucleic acid components of the ligation reaction do not form self-ligation products: The results also show a band of the appropriate size (75 bases) in the complete reaction to be the expected product of the cPT7IVS15 and RNA$_{35}$ ligation (DNA:RNA hybrid).

Example 2: Three Different Ligases Will Ligate Double Stranded DNA to RNA

All ligation reaction components except the ligase enzymes were mixed as indicated in Table 2. The reactions were heated at 60° C. for five minutes and allowed to cool to room temperature. Different ligase enzymes were added to the appropriate tubes and the reactions incubated at 30° C. for two hours. Each reaction was stopped by the addition of 1 μl RNase-free 0.5 M EDTA (US Biochemicals, Inc.).

TABLE 2

Ligation reaction formulations for Example 2. 10X ligation buffers were supplied with the enzymes.

| Component | ID 1 | 2 | 3 | 4 | 5 | 6 | 7 | 8 |
|---|---|---|---|---|---|---|---|---|
| Water | 10 μl | 9 μl | 12 μl | 11 μl | 12 μl | 11 μl | 13 μl | 12 μl |
| 10X E. coli Ligase Buffer | 2 μl | 2 μl | | | | | | |
| 10X T4 DNA Ligase Buffer | | | 2 μl | 2 μl | | | | |
| 10X T4 RNA Ligase Buffer | | | | | 2 μl | 2 μl | 2 μl | 2 μl |
| SUPERASE.IN ™ (Ambion 20 Units/μl) | 1 μl | 1 μl | 1 μl | 1 μl | 1 μl | 1 μl | 1 μl | 1 μl |
| 5 mM NAD | 2 μl | 2 μl | | | | | | |
| PT7IVS15 (15 pmol/μl) | 1 μl | 1 μl | 1 μl | 1 μl | 1 μl | 1 μl | | |
| cPT7IVS15 (15 pmol/μl) | 1 μl | 1 μl | 1 μl | 1 μl | 1 μl | 1 μl | 1 μl | 1 μl |
| RNA$_{35}$ (16 pmol/μl) | 3 μl | 3 μl | 3 μl | 3 μl | 3 μl | 3 μl | 3 μl | 3 μl |
| E. coli Ligase (NEBL 10 Units/μl) | | 1 μl | | | | | | |
| T4 DNA Ligase (NEBL 400 Units/μl) | | | | 1 μl | | | | |
| T4 RNA Ligase (NEBL 10 Units/μl) | | | | | | | 1 μl | 1 μl |
| Total Volume | 20 μl | 20 μl | 20 μl | 20 μl | 20 μl | 20 μl | 20 μl | 20 μl |

Five microliter samples of every reaction were mixed with 5 μl of Gel Loading Buffer II (Ambion) and heat denatured at 95° C. for two minutes. The entire amount of each sample was loaded into separate wells of a 15% acrylamide, 7M urea TBE gel (Invitrogen) and subjected to electrophoresis at room temperature following the manufacturer's recommendations. Samples were loaded in numerical order from left to right, respectively, with DNA molecular weight makers interspersed. Electrophoresis was stopped when the BPB loading dye was at the bottom of the gel. The gel was stained by soaking in a 1:200 dilution of SYBR™ Gold Dye (Molecular Probes) in water for 10 minutes. After staining the gel was rinsed in distilled water and the DNA bands visualized by scanning in a TYPHOON™ (GE Healthcare Bio-sciences). The gel was scanned using the same parameters as in Example 1.

The results show ligation products were produced indicating that all three ligases function to ligate a DNA 5'-phosphate group to an RNA 3'-hydroxyl group. No ligation product was seen in reaction lacking the PT7IVS15 oligo.

Example 3: Ligated RNA can be Transcribed

All ligation reaction components except *E. coli* DNA Ligase were mixed as indicated in Table 3. The reactions were heated at 60° C. for five minutes and allowed to cool to room temperature. *E. coli* DNA Ligase was added to the appropriate tubes and the reactions incubated at 16° C. for two hours. Each reaction was stopped by the addition of 1 μl RNase-free 0.5 M EDTA (US Biochemicals, Inc.).

TABLE 3

Ligation reaction formulations for Example 3.

| Component↓/ID→ | 1 | 2 | 3 | 4 |
|---|---|---|---|---|
| Water | 12 μl | 11 μl | 12 μl | 11 μl |
| 10X *E.coli* Ligase Buffer | 2 μl | 2 μl | 2 μl | 2 μl |
| SUPERASE.IN ™ | 1 μl | 1 μl | 1 μl | 1 μl |
| PT7IVS5 (15 pmol/μl) | 1 μl | 1 μl | | |
| cPT7IVS5 (5 pmol/μl) | 1 μl | 1 μl | | |
| PT7IVS15 (15 pmol/μl) | | | 1 μl | 1 μl |
| cPT7IVS15 (5 pmol/μl) | | | 1 μl | 1 μl |
| RNA$_{35}$ (5 pmol/μl) | 3 μl | 3 μl | 3 μl | 3 μl |
| *E.coli* Ligase | | 1 μl | | 1 μl |
| Total Volume | 20 μl | 20 μl | 20 μl | 20 μl |

Five microliter samples of every reaction were mixed with 5 μl of Gel Loading Buffer II (Ambion) and heat denatured at 95° C. for two minutes. The entire amount of each sample was loaded into separate wells of a 15% acrylamide, 7M urea TBE gel (Invitrogen) and subjected to electrophoresis at room temperature following the manufacturer's recommendations. Samples were loaded in numerical order from left to right, respectively, with an RNA molecular weight maker (DECADE™ Markers from Ambion) in lane 1. Electrophoresis was stopped when the BPB loading dye was at the bottom of the gel. The gel was stained by soaking in a 1:200 dilution of SYBR™ Gold Dye (Molecular Probes) in water for 10 minutes. After staining the gel was rinsed in distilled water and the DNA bands visualized by scanning in a TYPHOON™ (GE Healthcare Bio-Sciences).

The gel was scanned using the same parameters as in Example 1. Expected ligation products were seen from reactions 2 and 4, respectively.

Amplification was accomplished using aliquots of reactions 2 and 4 and MEGASCRIPT™ T7 Kit (Ambion) as outlined in Table 4. All components were mixed together and incubated at 37° C. for one hour.

TABLE 4

Amplification reactions for Example 3.

| Component ↓/ID → | 1 | 2 | 3 | 4 |
|---|---|---|---|---|
| Water | 2.6 μl | 0.6 μl | 2.6 μl | 0.6 μl |
| 10x Reaction Buffer | 2 μl | 2 μl | 2 μl | 2 μl |
| SUPERASE.IN ™ | 1 μl | 1 μl | 1 μl | 1 μl |
| Example 3 Reaction 2 | 4 μl | 4 μl | | |
| Example 3 Reaction 4 | | | 4 μl | 4 μl |
| 20 mM MgCl$_2$ | 4 μl | 4 μl | 4 μl | 4 μl |
| 10 mM NTP Mix | 6.4 μl | 6.4 μl | 6.4 μl | 6.4 μl |
| 17 Enzyme Mix | | 2 μl | | 2 μl |
| Total Volume | 20 μl | 20 μl | 20 μl | 20 μl |

Following incubation, reactions 2 and 4 were each split into equal aliquots. One aliquot of each reaction had 0.5 μl 0.5 M EDTA added and were stored on ice until gel analysis. The remaining aliquots were heated at 70° C. for 5 minutes to inactivate the SUPERASE.IN™. Each heated aliquot had 1 μl of RNase A (44 Units; US Biochemical, Inc.) added and were incubated for 10 minutes at 37° C. The RNase digests were each stopped by the addition of 0.5 μl 0.5 M EDTA. Five microliter samples of every reaction were mixed with 5 μl of Gel Loading Buffer II (Ambion) and heat denatured at 95° C. for two minutes. The entire amount of each sample was loaded into separate wells of a 15% acrylamide, 7M urea TBE gel (Invitrogen) and subjected to electrophoresis at room temperature following the manufacturer's recommendations. Electrophoresis was stopped when the BPB loading dye was approximately 2 cm from the bottom of the gel. The gel was stained by soaking in a 1:200 dilution of SYBR™ Gold Dye (Molecular Probes) in water for 10 minutes. After staining the gel was rinsed in distilled water and the DNA bands visualized by scanning in a TYPHOON™ (GE Healthcare Bio-Sciences). The gel was scanned using the same parameters as in Example 1.

Transcription reaction products from reactions 2 and 5, respectively were, in general, typical of a T7 RNA polymerase (RNAP) reaction. A runoff transcript of the expected 9 nucleotides (nt) was observed situated above the BPB dye. This short runoff transcript results from unligated PT7IVS5 and cPT7IVS5 oligos carried over from the ligation reaction. T7 RNAP is known to perform a non-templated addition of one nucleotide in runoff reactions (Arnaud-Barbe, et al. 1998) and this was be seen just above the 9 nt product. Additionally, the RNAP, after binding to the double stranded DNA promoter, is also known to go through rounds of abortive transcription (Lopez, et al. 1997) until a long enough nascent transcript has been synthesized for the polymerase to clear the promoter. Abortive transcription products were observed below the 9 nt product in some reactions. Surprisingly, this reaction contains no runoff transcript in the expected size range of 44 nt. Instead a smear of RNA was observed higher in the gel that suggests a heterodisperse population of product sizes (non-specific products). An RNA smear disappeared upon treatment with RNase A but the DNA bands remained. This smearing is another trait of T7 RNAP (Macdonald, et al., J. Mol. Biol. 232:1030-1047 (1993) and results from the enzyme slipping forward and backward during polymerization along homopolymeric templates.

The same types of reaction products were observed in the transcriptions containing PT7IVS15 and cPT7IVS15 oligos (lane 6). An expected 19 nt runoff transcript from the carryover of unligated oligos from the ligation reaction were observed (arrow) as well as smaller abortive transcripts. However, the non-templated addition of a nt was obscured by what appears to be a stuttering of the polymerase as it enters the RNA portion of the DNA:RNA hybrid. Again, no expected transcript size of 75 nt was observed, but rather an RNA smear that disappeared with RNase A treatment. The RNA smear was denser in some reactions suggesting that the longer IVS allows the RNAP to enter the RNA portion of the DNA:RNA hybrid more efficiently.

Example 4: Double Stranded DNA to mRNA

All components were mixed as indicated in Table 5 and incubated at 30° C. for 15 minutes. There was no annealing step included in this example. Besides ligation of cPT7IVS15 to RNA$_{35}$, skeletal muscle polyA RNA (smRNA; Russian Cardiology Research and Development Center) was also used as a ligation target for this system. Each reaction was stopped by the addition of 1 μl RNase-free 0.5 M EDTA (US Biochemicals, Inc.).

TABLE 5

Ligation reaction formulations for Example 4. The 10x Ligation Buffer and T4 DNA Ligase were certified RNase-free and supplied by Takara.

| Component ↓/ID → | 1 | 2 | 3 | 4 | 5 |
|---|---|---|---|---|---|
| Water | 3.9 μl | 6.6 μl | 2.9 μl | 3.9 μl | 2.9 μl |
| 10x Ligation Buffer | 2 μl | 2 μl | 2 μl | 2 μl | 2 μl |
| SUPERASE.IN ™ | 1 μl | 1 μl | 1 μl | 1 μl | 1 μl |
| PT7IVS15 (15 pmol/μl) | 1 μl | | 1 μl | 1 μl | 1 μl |
| cPT7IVS15 (5 pmol/μl) | 2.7 μl | | 2.7 μl | 2.7 μl | 2.7 μl |
| smRNA (1 μg/μl) | 1 μl | 1 μl | 1 μl | | |
| RNA$_{35}$ (16 pmol/μl) | | | | 1 μl | 1 μl |
| 50% PEG 8000 | 8.4 μl | 8.4 μl | 8.4 μl | 8.4 μl | 8.4 μl |
| 14 DNA Ligase (350 Units/μl) | | 1 μl | 1 μl | | 1 μl |
| Total Volume | 20 μl | 20 μl | 20 μl | 20 μl | 20 μl |

Five microliter samples of every reaction were mixed with 5 μl of Gel Loading Buffer II (Ambion) and heat denatured at 95° C. for two minutes. The entire amount of each sample was loaded into separate wells of a 15% acrylamide, 7M, urea TBE gel (Invitrogen) and subjected to electrophoresis at room temperature following the manufacturer's recommendations. Electrophoresis was stopped when the BPB loading dye was approximately 2 cm from the bottom of the gel. The gel was stained by soaking in a 1:200 dilution of SYBR™ Gold Dye (Molecular Probes) in water for 10 minutes. After staining the gel was rinsed in distilled water and the DNA bands visualized by scanning in a TYPHOON™ (GE Healthcare Bio-Sciences). The gel was scanned using the same parameters as in Example 1.

The expected ligation product of the oligos with the RNA$_{35}$ was seen.

Amplification was carried out using aliquots of reactions 1 and 3 and MEGASCRIPT™ T7 Kit (Ambion) as outlined in Table 6. All components were mixed together and incubated at 37° C. for one hour.

TABLE 6

Reactions for Example 3.

NTP Mix

| Component | |
|---|---|
| 75 mM ATP | 2.8 μl |
| 75 mM CTP | 2.8 μl |
| 75 mM GTP | 2.8 μl |
| 75 mM UTP | 2.8 μl |
| Total Volume | 11.2 μl |

Rxn Setup

| Component ↓/ID → | 1 | 2 |
|---|---|---|
| NTP Mix | 11.2 μl | 11.2 μl |
| Water | 15.8 μl | 15.8 μl |
| 10x Transcription Buffer | 4 μl | 4 μl |
| SUPERASE.IN ™ | 1 μl | 1 μl |

TABLE 6-continued

Reactions for Example 3.

| | | |
|---|---|---|
| Ligation #1 | 4 μl | |
| Ligation #3 | 4 μl | |
| T7 Enzyme Mix | 4 μl | 4 μl |
| Total Volume | 40 μl | 40 μl |

The reactions were each stopped by the addition of 1 μl 0.5 M EDTA. Five microliter samples of every reaction were mixed with 5 μl of Gel Loading Buffer II (Ambion) and heat denatured at 95° C. for two minutes. The entire amount of each sample was loaded into separate wells of a 15% acrylamide, 7M urea TBE gel (Invitrogen) and subjected to electrophoresis at room temperature following the manufacturer's recommendations. Electrophoresis was stopped when the BPB loading dye was approximately 2 cm from the bottom of the gel. The gel was stained by soaking in a 1:200 dilution of SYBR™ Gold Dye (Molecular Probes) in water for 10 minutes. After staining the gel was rinsed in distilled water and the DNA bands visualized by scanning in a TYPHOON™ (GE Healthcare Bio-Sciences). The gel was scanned using the same parameters as in Example 1.

The results show both run off and abortive transcripts as well as a single base non-templated nucleotide addition, much as was observed in Example 3. The RNA smear at the top of the gel in some reactions, along with the relative decrease in intensity of the runoff transcript when compared to lane 1, suggests the capability of this system to both anneal to, ligate a double stranded DNA RNAP promoter to and transcribe complementary RNA from a DNA:mRNA hybrid.

Example 5: Fast Ligation Kinetics

Ligation reactions were prepared as outlined in Table 7. A bulk mix was prepared containing all components of the reaction except T4 DNA ligase and 19 μl aliquoted into each of 7 tubes. The zero time point had 1 μl of water and 1 μl 0.5 M EDTA added and was stored on ice until gel analysis. All remaining reactions had 1 μl T4 DNA Ligase (350 Units; Takara) added and were incubated at room temperature for between 30 seconds (") and 8 minutes ('). At the indicated time interval 1 μl of 0.5 M EDTA was added to the appropriate tube and the reaction placed on ice until gel analysis.

TABLE 7

Formulation of the bulk mix and reaction time intervals for Example 5.

| Component | 1X | 8X |
|---|---|---|
| Water | 10.3 μl | 82.4 μl |
| 10X Ligation Buffer | 2 μl | 16 μl |
| SUPERASE.IN ™ | 1 μl | 8 μl |
| PT7IVS15 (15 pmol/μl) | 1 μl | 8 μl |
| cPT7IVS15 (5 pmol/μl) | 2.7 μl | 21.6 μl |
| RNA$_{35}$ (16 pmol/μl) | 1 μl | 8 μl |
| smRNA (1 μg/μl) | 1 μl | 8 μl |
| Total Volume | 19 μl | 152 μl |

| Time Points | | | | | | |
|---|---|---|---|---|---|---|
| 0 | 30" | 60" | 90" | 2' | 4' | 8' |

Five microliter samples of every reaction were mixed with 5 μL of Gel Loading Buffer II (Ambion) and heat denatured at 95° C. for two minutes. The entire amount of each sample was loaded into separate wells of a 15% acrylamide, 7M urea TBE gel (Invitrogen) and subjected to electrophoresis at room temperature following the manufacturer's recommendations. Electrophoresis was stopped when the BPB loading dye was at the bottom of the gel. The gel was stained by soaking in a 1:200 dilution of SYBR™ Gold Dye (Molecular Probes) in water for 10 minutes. After staining the gel was rinsed in distilled water and the DNA bands visualized by scanning in a TYPHOON™. The gel was scanned using the same parameters as in Example 1.

The appearance of the cPT7IVS15 RNA$_{35}$ ligation product in as little as 30 seconds and the fact that this ligation product did not appear to increase in intensity over time suggests very rapid reaction kinetics.

Example 6: Amplification Yields Improve with the Addition of Either EDTA or Citrate Oligos used in the ligations for this example were first mixed together as outlined in Table 8. Ligation reactions were then prepared as outlined in Table 9. The ligations were mixed and incubated at 30° C. for 15 minutes. Ligation number 1 had 1 μl of 0.5 M EDTA added, while ligations 2-4 each had 2 μl 0.5 M EDTA added. Ligations 2-4 were pooled together and mixed well.

TABLE 8

Mixture of oligos for Example 6.

| Component | 1X | 10x |
|---|---|---|
| PT7IVS15 (15 pmol/μl) | 1 μl | 10 μl |
| cPT7IVS15 (5 pmol/μl) | 2.7 μl | 27 μl |
| Total Volume | 3.7 μl | 37 μl |

TABLE 9

Ligation reactions for Example 6.

| Component /ID → | 1 | 2 | 3 | 4 |
|---|---|---|---|---|
| Water | 14.6 μl | 28.6 μl | 28.6 μl | 28.6 μl |
| 10X Ligation Buffer | 2 μl | 4 μl | 4 μl | 4 μl |
| SUPERASE.IN ™ | 1 μl | 2 μl | 2 μl | 2 μl |
| Oligo Mix (Table 8) | 1.4 μl | 1.4 μl | 1.4 μl | 1.4 μl |
| smRNA (1 μg/μl) | 1 μl | 2 μl | 2 μl | 2 μl |
| 14 DNA Ligase (350 units/μl) | | 2 μl | 2 μl | 2 μl |
| Total Volume | 20 μl | 40 μl | 40 μl | 40 μl |

Amplification was accomplished using aliquots of the ligation reactions and MEGASCRIPT™ T7 Kit (Ambion) as outlined in Table 10. All components were mixed together and incubated at 37° C. for one hour. Each reaction was stopped by the addition of 2 μl 0.5 M EDTA.

TABLE 10

Reactions for Example 6.

| Component ID→ | 1 | 2 | 3 | 4 | 5 | 6 | 7 | 8 | 9 |
|---|---|---|---|---|---|---|---|---|---|
| Water | 15.8 μl | 15.8 μl | 14.8 μl | 14.8 μl | 13.8 μl | 14.8 μl | 13.8 μl | 11.8 μl | 7.8 μl |
| NTP Mix (as Example 4) | 11.2 μl | 11.2 μl | 11.2 μl | 11.2 μl | 11.2 μl | 11.2 μl | 11.2 μl | 11.2 μl | 11.2 μl |
| 304 mM Citrate | | | 1 μl | | 1 μl | | | | |
| 324 mM DTT | | | | 1 μl | 1 μl | | | | |
| 20 mM EDTA | | | | | | 1 μl | 2 μl | 4 μl | 8 μl |
| 10X Transcription Buffer | 4 μl | 4 μl | 4 μl | 4 μl | 4 μl | 4 μl | 4 μl | 4 μl | 4 μl |
| SUPERASE.IN ™ | 1 μl | 1 μl | 1 μl | 1 μl | 1 μl | 1 μl | 1 μl | 1 μl | 1 μl |
| Ligation #1 | 4 μl | | | | | | | | |
| Ligation 2 + 3 + 4 | | 4 μl | 4 μl | 4 μl | 4 μl | 4 μl | 4 μl | 4 μl | 4 μl |
| T7 Enzyme Mix | 4 μl | 4 μl | 4 μl | 4 μl | 4 μl | 4 μl | 4 μl | 4 μl | 4 μl |
| Total Volume | 40 μl | 40 μl | 40 μl | 40 μl | 40 μl | 40 μl | 40 μl | 40 μl | 40 μl |

Figure 4:
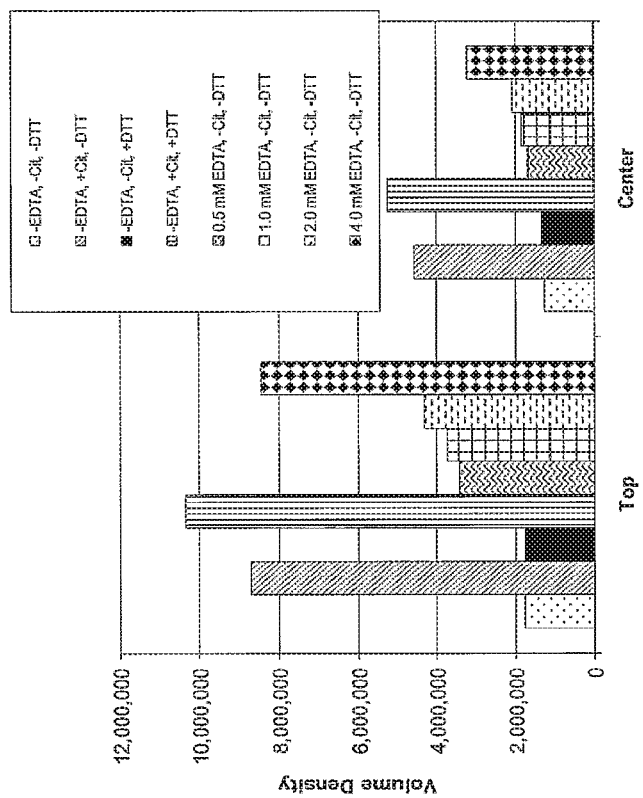
FIG. 4 shows results of volume density measurements.
Figure 8:
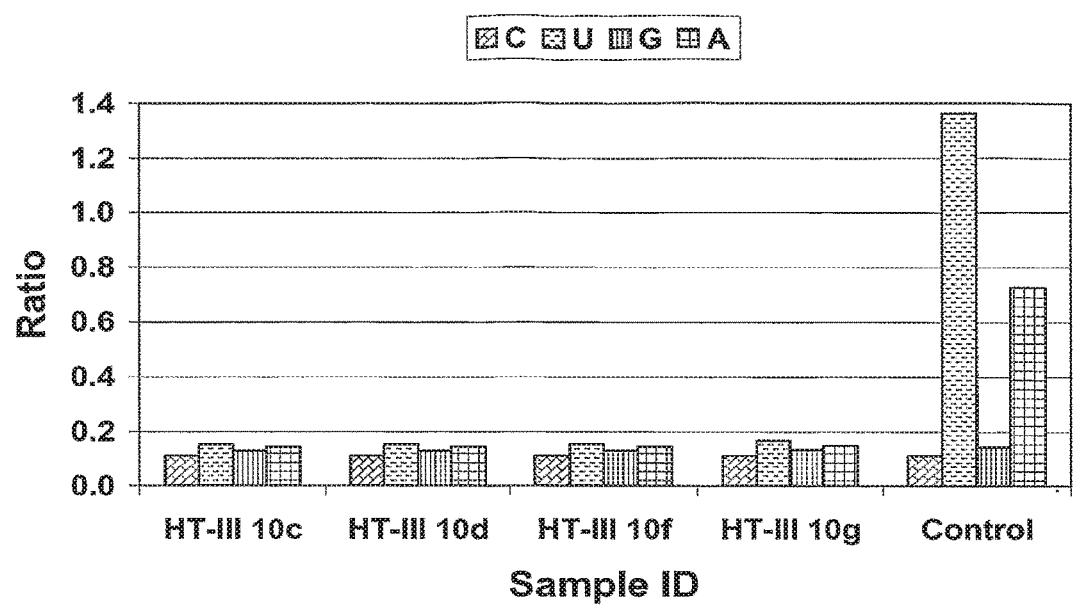
FIG. 8 shows results obtained from HPLC analysis of exonuclease digested cRNA. All results were normalised to 'C'.

Gel analysis was as outlined for Example 5 using a 6% 7M urea TBE gel (Invitrogen). The BPB dye was run to the bottom of the gel. FIG. 8 is the fluorescent of the gel that was boxed off for volume density analysis using IMAGEQUANT™ Version 5.2 software (GE Healthcare Bio-Sciences). The gel was scanned using the same parameters as in Example 1. The Results are Shown in FIG. 4.

Surprisingly, both citrate and EDTA were observed to stimulate yields from amplification reactions, as evidenced by an increase in volume density, using RNA as the template. Results suggest that other compounds observed to stimulate amplification reaction yields on DNA templates would also function with RNA templates. These compounds would include polyamine (US 2003/0073202) and nitrirotriacetic acid, uramil diacetic acid, trans-1,2-cyclohexanediaminetetraacetic acid, diethylenetriamine-pentaacetic acid, ethylene glycol bis(2-aminoethyl)ether diaminetetraacetic acid, triethylenetetraminehexaacetic acid and their salts (U.S. Pat. No. 6,261,773). Additionally, other compounds with the ability to chelate metal ions, e.g., isocitrate, trans-1,2-diaminocyclohexanetetraacetic acid, and (ethylene-dioxy)diethylenedinitrilotetraacetic acid, would also be expected to stimulate yields from amplification reactions when used at the proper concentration.

Example 7: Replication Kinetics in the Presence of EDTA

A kinetic study of amplification reactions in the presence or absence of EDTA was completed. Additionally, all the reactions contained biotin-11-UTP (Perkin Elmer Life Sciences). Ligations and replication reactions were prepared as outlined in Table 11 A-C. The ligations were mixed and incubated at 30° C. for 15 minutes and then 60° C. for 10 minutes to heat-kill the ligase. Bulk replication reactions were prepared with or without EDTA. Aliquots of 20 µL of each bulk mix were distributed to tubes for incubation. Zero time points immediately had 1 µl each of 0.5 M EDTA added and were stored at −80° C. The remaining tubes were incubated for the following time intervals at 37° C.: 1, 2, 4, 8, or 16 hours. Each reaction was stopped by the addition of 1 µl of 0.5 M EDTA and stored at −80° C. until gel analysis (data not shown) and purification. Each reaction was purified by using MICROCON™ YM-30 filter units (Millipore) according to the manufacturer's instructions. Following purification aliquots of each reaction had the absorbance determined at 260 nm. RNA yields were determined by multiplying the absorbance reading times the dilution times 40 µg/ml

TABLE 11

Ligation and Replicationreactions for Example 7.

A. Oligo Mixture for Example 7.

| Component ↓ | 1X | 10X |
|---|---|---|
| PT7IVS15 (15 pmol/µl) | 1 µl | 10 µl |
| cPT7IVS15 (5 pmol/µl) | 2.7 µl | 27 µl |
| Total Volume | 3.7 µl | 37 µl |

B. Ligation Reactions for Example 7.

| Component ↓/ID → | L1 |
|---|---|
| Water | 44 µl |
| 10X Ligation Buffer | 6 µl |
| SUPERASE.IN ™ | 2 µl |
| Oligo Mix | 2 µl |
| smRNA (1 µg/µl) | 3 µl |
| T4 DNA Ligase (350 units/µl) | 3 µl |
| Total Volume | 60 µl |

TABLE 11-continued

Ligation and Replicationreactions for Example 7.

C. Reaction preparation for Example 7.
NTP Master Mix

| Component | Volume |
|---|---|
| 75 mM ATP | 36 µl |
| 75 mM CTP | 36 µl |
| 75 mM GTP | 36 µl |
| 75 mM UTP | 28.8 µl |
| Biotin-11-UTP | 54 µl |
| Total Volume | 190.8 µl |

Reaction Master Mixes

| Component ↓/ID → | A | B |
|---|---|---|
| Water | 14 µl | 7 µl |
| 80 mM EDTA | none | 7 µl |
| NTP Mix | 74.2 µl | 74.2 µl |
| 10X Transcription Buffer | 14 µl | 14 µl |
| SUPERASE.IN ™ | 7 µl | 7 µl |
| Ligation L1 | 16.8 µl | 16.8 µl |
| T7 RNAP Mix | 14 µl | 14 µl |
| Total Volume | 140 µl | 140 µl |

The results showed an increase in RNA yield over several hours and also that RNA yield was increased at the 8 and 16 hour time points in the presence of EDTA.

Example 8: HPLC Analysis of Replication Products

Products from Ligation-Based RNA Amplification reactions were analyzed by simultaneous digestion with two different RNA exonucleases and analyzed by HPLC. Digestions of 10 µg amplified RNA (cRNA) with both 2 µg snake venom phosphodiesterase and 0.6 Units bacterial alkaline phosphatase (both from GE Healthcare Bio-sciences) were performed in 50 mM HEPES buffer, pH 8, and 15 mM $MgCl_2$ for 6 hours at 37° C. Additionally, 4 mM solutions of each nucleoside triphosphate were also digested as a reference. After digestion, the 60 µl reaction volumes were brought to 120 µl with water and purified using 0.2 µm nylon ACRODISC™ syringe filters (Pall Life Sciences) to remove protein. Each digestion had between 20-40 µl injected into an HPLC connected to an XTERRA® MS C18 5 µm 4.6×100 mm column (Waters) with the buffer gradient profile in Table 12. Buffer A was 0.1% triethyl ammonium acetate (Applied Biosystems, Inc.) and Buffer B was acetonitrile (VWR Scientific).

TABLE 12

Gradient Table for Nucleoside Analysis by HPLC in Example 8.

| | Time (min) | Flow (ml/min) | % A | % B |
|---|---|---|---|---|
| 1 | 0 | 0.70 | 100.0 | 0.0 |
| 2 | 10.00 | 0.70 | 95.0 | 5.0 |
| 3 | 11.00 | 0.70 | 90.0 | 10.0 |
| 4 | 13.00 | 0.70 | 70.0 | 30.0 |
| 5 | 14.00 | 0.70 | 0.0 | 100.0 |
| 6 | 17.00 | 0.70 | 0.0 | 100.0 |
| 7 | 18.00 | 0.70 | 100 | 0.0 |
| 8 | 27.00 | 0.70 | 100 | 0.0 |

Using this solvent system, the order of nucleoside elution, earliest to latest, was 'C', 'U', 'G', and 'A'. Original digestion data indicated that a non-specific product was synthesized when ligations and amplification reactions were performed as outlined in Example 6 Reaction 2 with incubation at 37° C. for 14 hours. This non-specific product was higher in 'A' and 'U' nucleosides as compared to control reactions performed using a DNA template.

The results showed HPLC traces between 2 minutes and 12 minutes of digested RNA for Example 8. A. Nucleosides only (used as a reference for elution time). B. Control reaction using a DNA template. C. Ligation-Based RNA Amplification material demonstrating a high 'A' and high 'U' non-specific product.

It was also observed that addition of either biotin-11-UTP or CY5™-UTP to Ligation-Based RNA Amplification reactions decreased the high 'U' peak of the non-specific product.

Decrease in the high 'U' peak in RNA exonuclease digested Ligation-Based RNA Amplification reactions when biotin-11-UTP was included. A 25% biotin-11-UTP data were generated using T3 RNA polymerase and oligos PT3w/T24 and cPT3. B 50% CY5™-UTP data were generated using T7 RNA polymerase.

Various NTP analogs were tested in Ligation-Based RNA Amplification reactions in an attempt to decrease the high 'A' peak observed in the RNA exonuclease digests. The analogs were substituted at concentrations between 100% and 20% with a concomitant decrease in the non-analog nucleoside. For example, if the nucleotide analog was substituted at a 25% concentration, then the corresponding nucleotide had its concentration dropped to 75%. Of the various analogs and concentrations tested (Table 13) only 2'-Amino-2'-deoxyadenosine-5'-Triphosphate and 2-Aminoadenosine-5'-Triphosphate (diaminopurine; DAP) were observed to decrease the high 'A' peak of the non-specific product.

TABLE 13

NTP analogs and concentrations tested for Example 8.

| NTP Analog | % Substitution of Corresponding NTP |
|---|---|
| 5-Bromouridine-5'-Triphosphate (SIGMA) | 25 |
| 5-Iodouridine-5'-Triphosphate (SIGMA) | 50, 25 |
| 5-Bromocytidine-5'-Triphosphate | 100, 75, 50, 25 |
| 5-Iodocytidine-5'-Triphosphate | 50, 25 |
| $N^6$-Methyladenosine-5'-Triphosphate | 75, 50, 25 |
| 2-Thiocytidine-5'-Triphosphate | 100, 75, 50, 25 |
| 2'-Amino-2'-deoxyadenosine-5'-Triphosphate | 100, 75, 50, 25 |
| 2'-Amino-2'-deoxycytidine-5'-Triphosphate | 75, 50, 25 |
| 2'-Azido-2'-deoxycytidine-5'-Triphosphate | 75, 50, 25 |
| 5-Methyluridine-5'-Triphosphate | 100, 75, 50, 25 |
| 2'-Amino-2'-deoxyuridine-5'-Triphosphate | 25 |
| 2'-O-methyluridine-5'-Triphosphate | 75, 50, 25 |
| 2'-O-methylpseudouridine-5'-Triphosphate | 75, 50, 25 |
| Inosine-5'-Triphosphate | 45, 22.5 |
| 2-Aminoadenosine-5'-Triphosphate | 75, 50, 25 |
| 5-Aminoallyluridine-5'-Triphosphate | 50, 25 |
| 2'-O-Methyl-5-methyluridine-5'-Triphosphate | 75, 50, 25 |

It was observed that a decrease in the high 'A' peak upon digestion with snake venom phosphodiesterase and bacterial alkaline phosphatase of Ligation-Based RNA Amplification reactions containing substitutions of either A 75% 2'-Amino-2'-deoxyadenosine-5'-Triphosphate (and 25% ATP) or B 50% diaminopurine (and 50% ATP). C shows the migration of DAP alone in this HPLC solvent system.

Whilst not being bound by theory it is possible that in the synthesis of poly 'A' poly 'U' non-specific products in the Ligation-Based RNA Amplification reaction products contained two parts: 1) the RNA polymerase slipped when transcribing the mRNA poly 'A' tail generating a poly 'U' RNA product, and 2) the poly 'U' RNA formed a duplex or triplex with the poly 'A' mRNA tail allowing the RNA polymerase to switch strands, transcribing the poly 'U' template and generating poly 'A' RNA. We predicted that by eliminating the poly 'U' from the strand switching reaction by adding a poly dA molecule to hybridize to it, the non-specific 'A' peak would disappear.

It was observed that was a decrease in non-specific 'A' peak with the addition of 6 µg poly $dA_{20}$ to the reaction as demonstrated by RNA exonuclease digestion and HPLC analysis of the resulting cRNA. Peak areas were normalized to 'C' before graphing. Control: reaction without biotin-UTP or $dA_{20}$. + B-UTP: reaction containing 25% biotin-UTP. + B-UTP + $dA_{20}$: reaction containing both 25% biotin-UTP and 6 µg poly $dA_{20}$.

Additionally, that adding a low concentration of a denaturant to the reaction also appeared to prevent the poly 'U' product from annealing to the template RNA with a resulting decrease in synthesis of poly 'A.' Results were obtained using RNA exonuclease digestion and resulting HPLC analysis when 0.0005% SDS was included in Ligation-Based RNA Amplification reactions.

The results showed a decrease in non-specific 'A' peak with the addition of 0.0005% SDS to the reaction as demonstrated by cRNA digestion with RNA exonuclease and HPLC analysis.

Example 9: Microarray Analysis of Transcribed Material

Ligations were prepared as outlined in Table 14, 'A' and 'B', using rat total RNA from both kidney and liver (Russian Cardiology Research and Development Center). Components were mixed and incubated at room temperature for 2 minutes. Ligations L1 and L2 each had 1 µl Lambda Exonuclease (20 units/µl; diluted from 50 units/µl in 1× ligation buffer; NEBL) while ligations L3 and L4 each had 3 µl of Lambda Exonuclease added (T7 gene 6 protein also could be added here; data not shown). All ligations were then placed at 37° C. and incubated for 30 minutes. Ligations L1 and L2 each had 1.6 µL of 0.5 M EDTA (Ambion) added, while ligations L3 and L4 each had 4.8 µl of 0.5 M EDTA added. The ligations were then incubated for 15 minutes at 65° C. to heat-kill all the enzymes in the mixtures. Following these manipulations the total volumes were now 16.5 µl each for L1 and L2 or 49.5 µl each for L3 and L4 with an EDTA concentration in each equal to approximately 48.48 mM.

TABLE 14

Ligations for Example 9.

A. Oligo Mix

| Component | Amt |
|---|---|
| OHThioPT7IVS25 (15 pmol/µl) | 10 µl |
| cPT7-PIVS25 (15 pmol/µl) | 10 µl |
| Water | 17.5 µl |
| Total Volume | 37.5 µl |

TABLE 14-continued

Ligations for Example 9.

B. Reactions

| Component ↓/ID → | L1 (X1) | L2 (X1) | L3 (X3) | L4 (X3) |
|---|---|---|---|---|
| Water | 7.7 μl | 7.7 μl | 18.3 μl | 18.3 μl |
| 10x Ligation Buffer | 1.6 μl | 1.6 μl | 4.8 μl | 4.8 μl |
| RNASIN ™ | 1.6 μl | 1.6 μl | 4.8 μl | 4.8 μl |
| Oligo Mix | 1 μl | 1 μl | 3 μl | 3 μl |
| Rat Kidney Total RNA (1 μg/μl) | 1 μl | | 3 μl | |
| Rat Liver Total RNA (1 μg/μl) | | 1 μl | | 3 μl |
| Bacterial Control mRNA | 1 μl | 1 μl | 3 μl | 3 μl |
| T4 DNA Ligase (Takara #K2071BC) | | | 4.8 μl | 4.8 μl |
| Total Volume | 13.9 μl | 13.9 μl | 41.7 μl | 41.7 μl |

Reactions were prepared as outlined in Table 15 using the ligated material prepared in Table 14. Reagents used in the reactions were from CODELINK™ Expression Assay Reagent Kit, Manual Prep (GE Healthcare), except the 10× Buffer. The 10× buffer used in this example was composed of 400 mM Tris-HCl, pH 8.0 (Ambion), 300 mM $MgCl_2$ (Ambion), 100 mM dithiothreitol (US Biochemical), and 20 mM spermidine (SIGMA). An 8× master mix of NTPs, biotin-11-UTP, 10× Buffer, $dA_{20}$ and T7 RNA polymerase was prepared based upon the 1× formulation in Table 15 A. Master Mix. This master mix was then aliquoted as outlined in Table 15 B. Reactions. Each reaction was incubated at 37° C. for 14 hours.

When the incubations were complete, each reaction was purified using an RNEASY™ Column (Qiagen) according to the manufacturer's instructions. An aliquot of each reaction was diluted either 1:7.5 (L1 and L2) or 1:30 (L3-L6) in water and the absorbance determined at 260 nm. FIG. 16 demonstrates the cRNA yields from each reaction assuming that 1 A260 unit of RNA contains 40 μg/mL of material.

The results showed the yields of cRNA obtained from reactions in Example 9.

Four micrograms from reactions L3-L6 or as much volume as possible from L1 and L2 were prepared for hybridization and hybridized to CODELINK™ ADME Rat Bioarray's (GE Healthcare) according to the manufacturer's instructions found in "CODELINK™ Gene Expression System: 16—Assay Bioarray Hybridization and Detection" rev. AA/2004-07 (GE Healthcare). Hybridizations were incubated at 37° C. for just over 19 hours with shaking at 250 rpm. When the hybridizations were complete, each chamber was washed three times with 250 μl of 46° C. 0.75× TNT buffer (1× TNT Buffer is 0.1 M Tris-HCl, pH 7.6, 0.15 M NaCl and 0.05% Tween 20). Following the washes, 250 μl on 46° C. 0.75× TNT Buffer was added to each chamber, the slides sealed and incubated at 46° C. for no longer than 10 minutes. The 0.75× TNT Buffer was removed and each chamber washed once with 250 μl of CY5™-Streptavadin conjugate (GE Healthcare) in TNB Buffer prepared as outlined in Table 16. TNB Buffer is 0.1 M Tris-HCl, pH 7.6, 0.15 M NaCl and 0.5% NEN Blocking Reagent (Perkin Elmer). Following the wash, 250 μl of CY5™-Streptavadin conjugate (GE Healthcare) in TNB Buffer was added to each chamber, the slides were sealed and incubated at ambient temperature in the dark for 30 minutes.

TABLE 15

Reactions prepared using the ligated material from Table 14.

A. Master Mix

| Component | X1 | X8 |
|---|---|---|
| Water | 0.5 μl | 4 μl |
| 75 mM ATP | 4 μl | 32 μl |
| 75 mM CTP | 4 μl | 32 μl |
| 75 mM GTP | 4 μl | 32 μl |
| 75 mM UTP | 3 μl | 24 μl |
| 10 mM Biotin-11-UTP (PE Life Sciences) | 7.5 μl | 60 μl |
| 10X Buffer | 5 μl | 40 μl |
| $dA_{20}$ (IDT; 6 μg/μl) | 0.5 μl | 4 |
| T7 RNAP Mix | 4 μl | 32 μl |
| Total Volume | 32.5 μl | 260 μl |

B. Reactions

| Component ↓/ID → | T1 | T2 | T3 | T4 | T5 | T6 |
|---|---|---|---|---|---|---|
| Water | 1 μl | 1 μl | 1 μl | | 1 μl | |
| 8X Master Mix | 32.5 μl | 32.5 μl | 32.5 μl | 32.5 μl | 32.5 μl | 32.5 μl |
| Ligation L1 | 16.5 μl | | | | | |
| Ligation L2 | | 16.5 μl | | | | |
| Ligation L3 | | | 16.5 μl | 16.5 μl | | |
| Ligation L4 | | | | | 16.5 μl | 16.5 μl |
| 0.025% SDS | | | | 1 μl | | 1 μl |
| Total Volume | 50 μl | 50 μl | 50 μl | 50 μl | 50 μl | 50 μl |

TABLE 16

Preparation of the CY5 ™-Streptavadin Conjugate in TNB Buffer
for one CODELINK ™ ADME rat Bioarray (16 wells).

| Component | Amt |
|---|---|
| TNB Buffer | 8.8 ml |
| CY5 ™-Streptavadin Conjugate | 17.6 µl |

Following conjugation of the CY5™-Streptavadin, each chamber was washed three times with 250 µL each of ambient temperature 0.75× TNT Buffer. Following the last wash, each chamber had 250 µl of ambient temperature 0.75× TNT Buffer added, the slides were sealed and incubated for 20 minutes at ambient temperature in the dark. The final wash was 250 µl of 0.1×SSC Buffer (Ambion) containing 0.05% Tween 20. This wash was added to each chamber and immediately removed. The slides were dried and scanned using an Axon Instruments GENEPIX® 4000B array scanner as outlined in "CODELINK™ Gene Expression System: 16—Assay Bioarray Hybridization and Detection" rev. AA/2004-07 (GE Healthcare). FIG. 17 shows the hybridization results for Example 9.

Figures 5A, 5B, 5C, 5D, 5E, 5F:
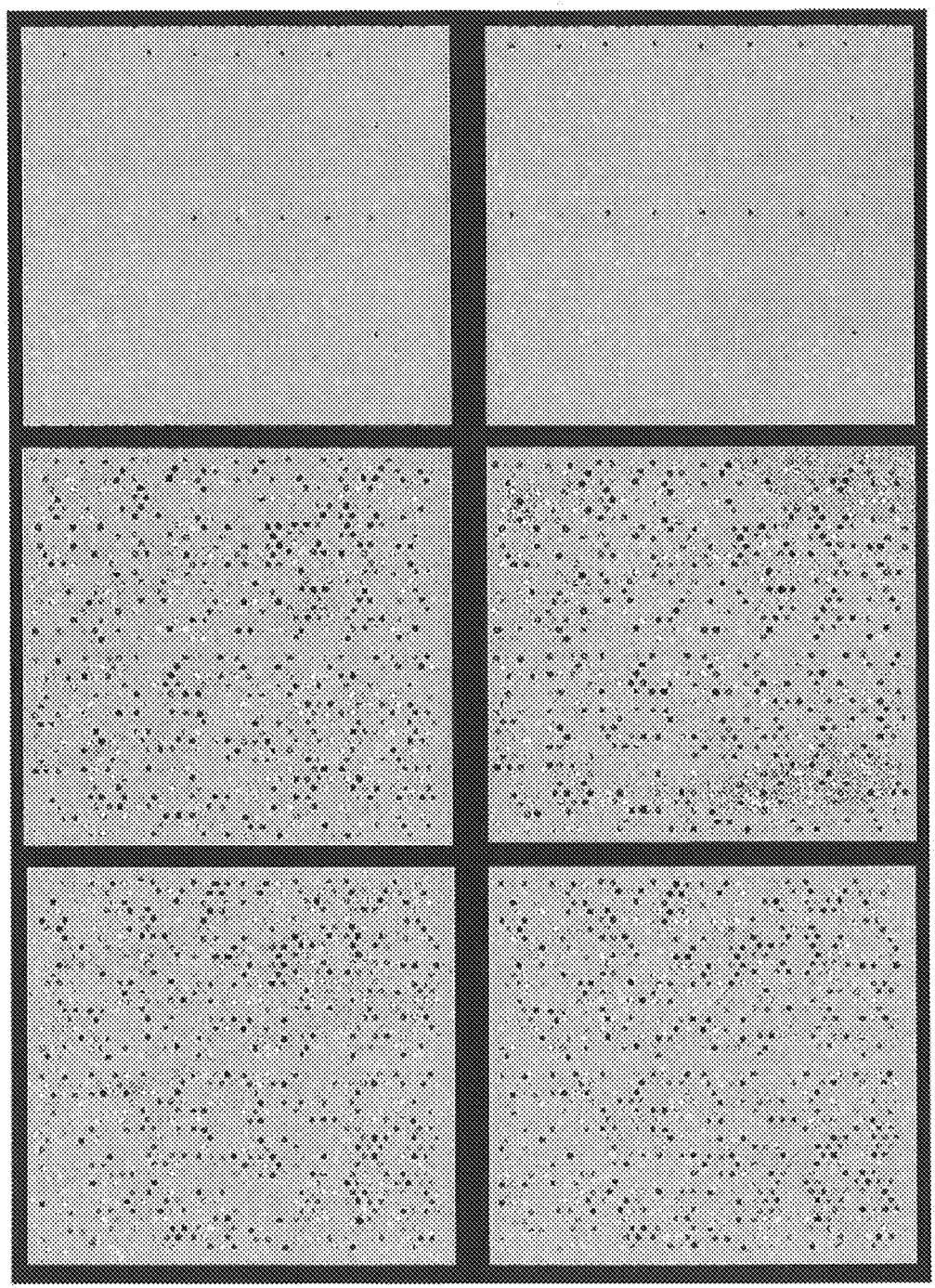

FIG. 5A shows Kidney Total RNA without ligase added to the ligation (T1), FIG. 5B shows Liver Total RNA without ligase added to the ligation (T2). FIG. 5C shows Kidney Total RNA plus ligase without SDS added to the reaction (T3). FIG. 5D shows Kidney Total RNA plus ligase with SDS added to the reaction (T4). FIG. 5E shows Liver Total RNA plus ligase without SDS added to the reaction (T5). FIG. 5F shows Liver Total RNA plus ligase with SDS added to the reaction (T5). Not all bioarray data are shown in these figures.

Figure 6:
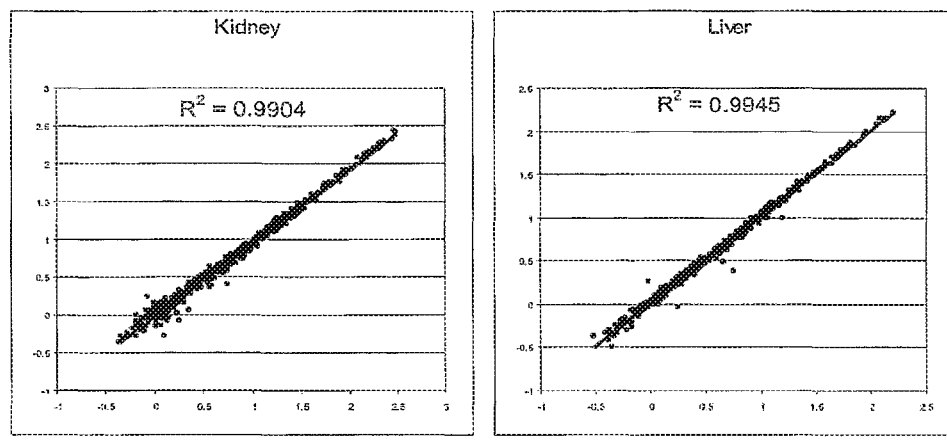
Figure 6:
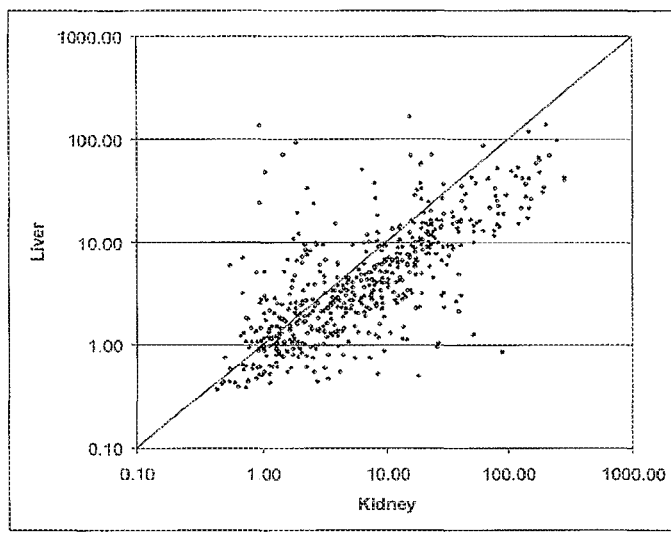
Figure 7:
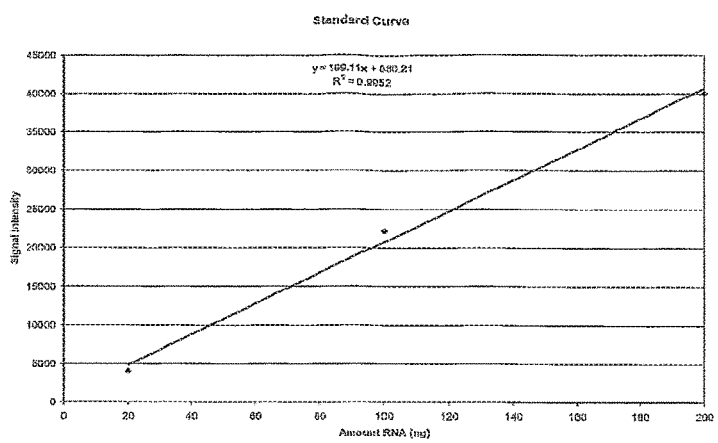
FIGS. 7A and 7B shows results of DNA and RNA before and after purification.
Figure 7:
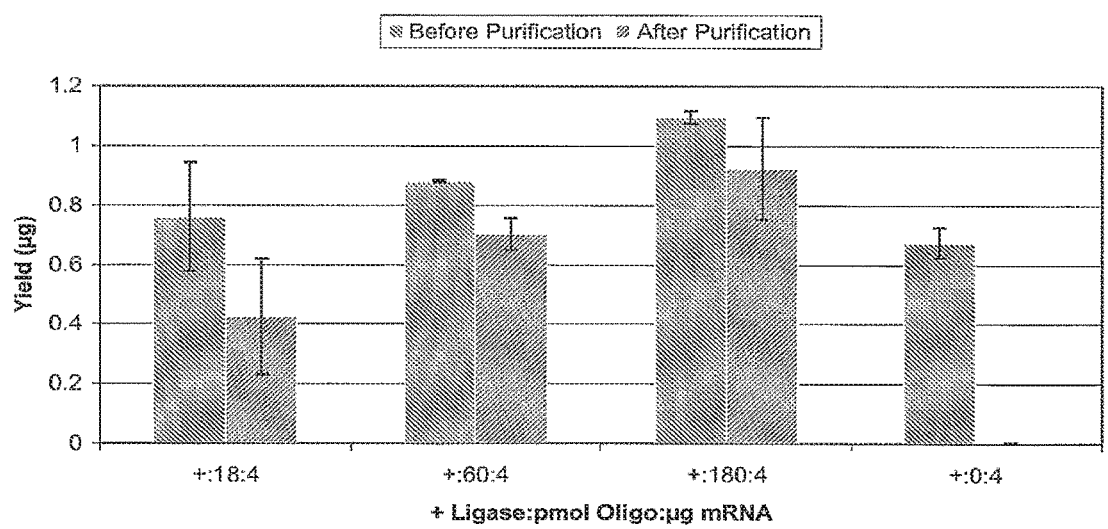

Signal intensities were determined on the ADME Rat Bioarrays using CODELINK™ Gene Expression Analysis software (GE Healthcare) according to the manufacturer's instructions. Expression levels were compared using average normalized signal intensities between arrays and the ratios derived thereof. The ratios were also used to determine differential expression levels between kidney and liver total RNA samples. Charts of these comparisons are found in FIGS. 6A and 6B, in which FIG. 6A shows the comparison between bioarrays using the same tissue with $r^2$ values, and FIG. 6B shows the differential expression comparison between liver and kidney bioarrays.

Example 10: Purification of mRNA Using Streptavidin Beads

Ligations were prepared as outlined in Table 17, mixed and incubated at ambient temperature for two minutes. Four microliters of Lambda Exonuclease were added to each tube and the reactions incubated at 37° C. for 15 minutes. Each tube had 6.4 µl of 0.5 M EDTA added and the reactions were incubated at 65° C. for 15 minutes. For each ligation to be purified, 100 µl of MPG Streptavidin magnetic particles (PureBiotech LLC) were washed once according to the manufacturer's instructions with 100 µl each 2 M KCl and then resuspended in 100 µl each of 2 M KCl and 82.5 µl each water. Each 182.5 µl preparation of washed magnetic beads had 17.5 µl of the appropriate ligation added and were incubated at ambient temperature for 15 minutes with occasional gentle mixing. The beads were separated from the liquid phase with a magnetic and washed twice with 200 µl each of 70% ethanol. Each bead pellet was resuspended in 50 µl of water and heated at 65° C. for 3 minutes. The beads were again separated from the liquid phase with a magnetic and the liquid phase saved for subsequent analysis.

TABLE 17

Ligations for Example 10.

| Component↓ ID→ | A | B | C | D | E | F |
|---|---|---|---|---|---|---|
| Water | 40.4 µl | 34.8 µl | 18.8 µl | 42.8 µl | 41.2 µl | 38.8 µl |
| 10X Ligation Buffer | 6.4 µl | 6.4 µl | 6.4 µl | 6.4 µl | 6.4 µl | 6.4 µl |
| RNASIN ™ | 6.4 µl | 6.4 µl | 6.4 µl | 6.4 µl | 6.4 µl | 6.4 µl |
| PT7w/T9 (15 pmol/λ) | 1.2 µl | 4 µl | 12 µl | | 4 µl | 4 µl |
| Biotin-cPT7-P (15 pmol/µl) | 1.2 µl | 4 µl | 12 µl | | 4 µl | 4 µl |
| smRNA (1 µg/µl, P921-128) | 4 µl | 4 µl | 4 µl | 4 µl | 4 µl | |
| T4 DNA Ligase | 6.4 µl | 6.4 µl | 6.4 µl | 6.4 µl | | 6.4 µl |
| Total Volume | 66 µl | 66 µl | 66 µl | 66 µl | 66 µl | 66 µl |

Nucleic acid concentrations (both DNA and RNA) were determined in the before and after purification samples using RIBOGREEN® RNA Quantitation Kit (Molecular Probes). RIBOGREEN® was diluted 1:200 in TE Buffer (Molecular Probes). The kit Ribosomal RNA (rRNA) Standard was diluted 1:50 in TE Buffer and a standard curve prepared as outlined in Table 18. Each before and after sample was diluted by mixing 17.5 µL with 82.5 µL TE Buffer. Ten microliters from each diluted sample were then each mixed with 90 µL TE Buffer and 100 µL RIBOGREEN®. Absorbance of the diluted samples in RIBOGREEN® and the standard curve were determined in a FARCYTE™ Fluorescent Plate Reader (GE Healthcare) using the manufacturer's default settings for fluorescein dye.

TABLE 18

Preparation of the Standard Curve for Example 10.

| Volume TE | 2 µg/ml rRNA Standard | Volume 1:200 RIBOGREEN ® | Amt RNA Added |
|---|---|---|---|
| 100 µl | None | 100 µl | Blank |
| 90 µl | 10 µl | 100 µl | 20 ng |
| 50 µl | 50 µl | 100 µl | 100 ng |
| None | 100 µl | 100 µl | 200 ng |

Example 11: RNase H Trimming of Poly(A) Tail

The workflow for this experiment was: 1) targeted trimming of the poly(A) tail of mRNA using RNase H (New England Biolabs; 10 Units/µl), 2) Ligation-Based Amplification of the trimmed poly(A) mRNA, and 3) selection of certain reactions for RNA exonuclease digestion and HPLC analysis. Trimming of the poly(A) tail of mRNA consisted of mixing either mRNA or total RNA (Russian Cardiology Research and Development Center) in separate reactions with oligos HT-III 10c, HT-III 10d, HT-III 10f or HT-III 10g in the presence of RNase H. A representative formula for the RNase H digestion is found in Table 19. RNase H was diluted in 1× Ligation Buffer to 2.5 Units/µl and digests were carried out at 37° C. for 30 minutes.

TABLE 19

A representative formulation for the trimming of the poly(A) tail from mRNA or mixed populations of RNA.

| Component ↓ | Volume | Volume |
|---|---|---|
| Water | 4.5 µl | 4 µl |
| 10X Ligation Buffer | 1 µl | 1 µl |
| 0.1% NP-40 (SIGMA) | 1 µl | 1 µl |
| mRNA (1 µg/µl) | 0.5 µl | |
| Total RNA (1 µg/µl) | | 1 µl |
| 10 µM Appropriate Oligo | 2 µl | 2 µl |
| RNase H | 1 µl | 1 µl |
| Total Volume | 10 µl | 10 µl |

Five microliters from each RNase H digestion were carried into separate, identically labeled, Ligation-Based RNA Amplification Reactions using the generalized reaction conditions in Table 20. Ligations were incubated at ambient temperature for 15 minutes and then each had 1 µl (5 Units) Lambda exonuclease added. After a 30 minute incubation at 37° C., each ligation had 1 µl of 129 mM EDTA added and was further incubated at 65° C. for 15 minutes. Reactions were prepared as generally outlined in Table 20 and incubated at 37° C. for 16 hours when 2 µl from each were analyzed by gel electrophoresis as in Example 5.

TABLE 20

Generalized ligation and amplification reactions for Example 11.

| A. Ligation Reactions | | B. Amplification Reactions | |
|---|---|---|---|
| Component ↓/ID → | 1X | Component ↓/ID → | 1x |
| Water | 1 µl | Water | 1.25 µl |
| 10X Ligation Buffer | 0.5 µl | 75 mm ATP | 1 µl |
| RNasin | 1 µl | 75 mm CTP | 1 µl |
| HT-III B5 (10 pmol/µl) | 1 µl | 75 mm GTP | 1 µl |
| cpT7'-IR15-(no A)5'-P (10 pmol/µl) | 1 µl | 75 mm UTP | 1 µl |
| | | 10X Buffer | 1 µl |
| RNase H Digestion Reaction | 5 µl | Ligation | 2.75 µl |
| T4 DNA Ligase (350 Units/µl) | 0.5 µl | T7 RNAP Mix | 1 µl |
| Total Volume | 10 µl | Total Volume | 10 µl |

Gel results indicated an increase in high molecular weight transcription products with RNase H added to the poly(A) trimming reactions from Table 19. These results showed all oligos capable of trimming the poly(A) tails from mRNA in both purified and mixed RNA populations. Additionally, the capture oligos HT-III B5 and cpT7'-IR15-(NoA)5'P were able to hybridize, ligate and transcribe this modified mRNA.

Purified products from representative reactions were digested with RNA exonucleases and analyzed by HPLC as outlined in Example 8. Included in these digests was a purified product from a reaction that did not have the poly(A) tail trimmed from the mRNA (labeled as 'Control'). FIG. 8 is a graph of the results of this HPLC analysis.

Results in FIG. 8 demonstrated that removing the poly(A) tail from mRNA prevented synthesis of high molecular weight artifacts during transcription. Additionally, material prepared as Example 11 has been shown to be functionally active in microarray hybridization experiments (data not shown).

It is apparent to those skilled in the art of the size of the poly(A) tail in mRNA can be determined by the methods described. If the nicking activity of RNaseH is moved three bases to the 5' end of the mRNA, the mRNA would be nicked at the message-poly(A) tail junction. The poly(A) tail length could then be sized by electrophoresis in a high percent (20%-30%) polyacrylamide denaturing gel.

All patents, patent publications, and other published references mentioned herein are hereby incorporated by reference in their entireties as if each had been individually and specifically incorporated by reference herein. While preferred illustrative embodiments of the present invention are described, one skilled in the art will appreciate that the present invention can be practiced by other than the described embodiments, which are presented for purposes of illustration only and not by way of limitation. The present invention is limited only by the claims that follow.

We claim:

1. A method of producing double-stranded cDNA comprising:
   a) supplying RNA other than poly A;
   b) supplying one or more DNA nucleic acids having a double-stranded region and a single-stranded 3' terminal region, wherein the DNA nucleic acid comprises a nucleotide sequence that can subsequently be used as a promoter sequence for RNA synthesis and a tag sequence which can be used to label the nucleic acid or manipulate the nucleic acid;
   c) hybridizing the single-stranded 3' terminal region of the DNA nucleic acid to the RNA and ligating one 5' end of the double-stranded region of the DNA nucleic acid to the 3' end of the RNA by enzymatic means to make a ligation product;
   d) transcribing the ligation product with RNA polymerase to produce a 5'-tagged cRNA;
   e) ligating the 3' end of the 5'-tagged cRNA with a second double-stranded DNA comprising a double-stranded region and a single-stranded region, wherein the second DNA comprises a nucleotide sequence that can subsequently be used as a promoter sequence for RNA synthesis and a tag sequence, to make a ligated cRNA-DNA molecule;
   f) transcribing the ligated cRNA-DNA molecule with RNA polymerase to produce multiple copies of an RNA molecule containing a tag sequence at the 5' and 3' end of the RNA molecule;
   g) hybridizing the 5' and 3' tagged RNA molecule with a DNA primer which is complementary to the sequence tag at the 3' end of the 5' and 3' tagged RNA molecule;
   h) incubating the product of step g) with reverse transcriptase and dNTPs to produce a single-stranded cDNA-RNA heteroduplex, wherein the 3' end of the cDNA molecule in the cDNA-RNA heteroduplex contains a sequence tag that is complementary to the 5' tag sequence in the RNA molecule in the heteroduplex;
   i) incubating the product of step h) with RNase; and
   j) incubating the product of step i) with a second single-stranded primmer, the sequence of which is complementary to the tag sequence at the 3' end of the single-stranded cDNA, and DNA polymerase to produce a double-stranded cDNA containing a sequence tag at each end.

2. The method of claim 1, wherein the sequence tags are different from each other.

3. The method of claim 1, wherein the transcribing of step d) and/or step f) is performed in a reaction comprising one or more nucleotide analogues.

4. The method of claim 1, in which the DNA nucleic acids of step b) further comprise an affinity tag, wherein the affinity tag can be used to purify the ligation product of step c).

* * * * *

SEQUENCE LISTING

<160> NUMBER OF SEQ ID NOS: 17

<210> SEQ ID NO 1
<211> LENGTH: 47
<212> TYPE: DNA
<213> ORGANISM: Artificial sequence
<220> FEATURE:
<223> OTHER INFORMATION: Synthetic oligonucleotide

<400> SEQUENCE: 1
gtaatacgac tcactatagg gagttttttt tttttttttt tttttt                47

<210> SEQ ID NO 2
<211> LENGTH: 27
<212> TYPE: DNA

<213> ORGANISM: Artificial sequence
<220> FEATURE:
<223> OTHER INFORMATION: Synthetic oligonucleotide

<400> SEQUENCE: 2
aaaactccct atagtgagtc gtattac                                 27

<210> SEQ ID NO 3
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 3
aaattaatac gactcactat agggagacca caacggtttt tttttttttt tttttttttt    60

<210> SEQ ID NO 4
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 4
aaaaccgttg tggtctccct atagtgagtc gtattaattt                   40

<210> SEQ ID NO 5
<211> LENGTH: 35
<212> TYPE: RNA
<213> ORGANISM: Artificial sequence
<220> FEATURE:
<223> OTHER INFORMATION: Synthetic oligonucleotide

<400> SEQUENCE: 5
uguuguuuuu uuuuuuuuuu uuuuuuuuuu uuuuu                        35

<210> SEQ ID NO 6
<211> LENGTH: 65
<212> TYPE: RNA
<213> ORGANISM: Artificial sequence
<220> FEATURE:
<223> OTHER INFORMATION: Synthetic oligonucleotide

<400> SEQUENCE: 6
uacaacgucg ugacugggaa acaaaaaaaa aaaaaaaaa aaaaaaaaaa aaaaaaaaaa    60
aaaaa                                                         65

<210> SEQ ID NO 7
<211> LENGTH: 60
<212> TYPE: DNA
<213> ORGANISM: Artificial sequence
<220> FEATURE:
<223> OTHER INFORMATION: Synthetic oligonucleotide

<400> SEQUENCE: 7
aaataattaa ccctcactaa agggagacca caacggtttt tttttttttt tttttttttt    60

<210> SEQ ID NO 8
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 8
aaaaccgttg tggtctccct ttagtgaggg ttaattattt            40

<210> SEQ ID NO 9
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 9
aaaaaaaaaa aaaaaaaaaa            20

<210> SEQ ID NO 10
<211> LENGTH: 40
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (40)..()
<223> OTHER INFORMATION: Biotin attached at 3' end

<400> SEQUENCE: 10
aaaaccgttg tggtctccct atagtgagtc gtattaattt            40

<210> SEQ ID NO 11
<211> LENGTH: 57
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: First two A residues are linked by
      phosphorothioate bonds

<400> SEQUENCE: 11
aaaaattaat acgactcact atagggagta ataggactca ctatagggtt tttttt            57

<210> SEQ ID NO 12
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: u residues at positions 1 to 3 contain 2'-O-
      methyl groups
<220> FEATURE:
<221> NAME/KEY: misc_feature
<222> LOCATION: (9)..(9)
<223> OTHER INFORMATION: v is degenerate base being only A, C or G
<220> FEATURE:
<221> NAME/KEY: misc_feature
<222> LOCATION: (10)..(10)
<223> OTHER INFORMATION: n residue at position 10  contain 2'-O-methyl
      group and base can be A. C, G or T

<400> SEQUENCE: 12 uuuttttttvn            10

<210> SEQ ID NO 13
<211> LENGTH: 10
<212> TYPE: DNA
<213> ORGANISM: Artificial Sequence

```
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: u residues at position 1 to 3 contain 2'-O-
      methyl groups
<220> FEATURE:
<221> NAME/KEY: misc_feature
<222> LOCATION: (9)..(9)
<223> OTHER INFORMATION: v at position 9 can be A, C or G
<220> FEATURE:
<221> NAME/KEY: misc_feature
<222> LOCATION: (10)..(10)
<223> OTHER INFORMATION: n at position 10 can be any of A, C,  G or T

<400> SEQUENCE: 13 uuutttttvn                                                                10

<210> SEQ ID NO 14
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(4)
<223> OTHER INFORMATION: u residues at position 1 to 4 contain 2'-O-
      methyl groups
<220> FEATURE:
<221> NAME/KEY: misc_feature
<222> LOCATION: (9)..(9)
<223> OTHER INFORMATION: v residues at position 9  can be A, C or G
<220> FEATURE:
<221> NAME/KEY: misc_feature
<222> LOCATION: (10)..(10)
<223> OTHER INFORMATION: n residue at position 10  can be A, C,  G or T
      and contains 2'-O-methyl group

<400> SEQUENCE: 14 uuuuttttvn                                                                10

<210> SEQ ID NO 15
<211> LENGTH: 44
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (43)..()
<223> OTHER INFORMATION: V at position 43 ia a degenerate base and can
      be A,C or G
<220> FEATURE:
<221> NAME/KEY: misc_feature
<222> LOCATION: (44)..(44)
<223> OTHER INFORMATION: n at position 44 is a degenerate base and can
      be A, C, G or T

<400> SEQUENCE: 15
cgcaaattaa tacgactcac tataggGaga ccacaacggt ttvn                           44

<210> SEQ ID NO 16
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 16
ccgttgtggt ctccctatag tgagtcgtat taatttgcg                                 39
```

```
<210> SEQ ID NO 17
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(5)
<223> OTHER INFORMATION: u residues at position 1 to 5 contain 2'-O-
      methyl groups
<220> FEATURE:
<221> NAME/KEY: misc_feature
<222> LOCATION: (9)..(9)
<223> OTHER INFORMATION: v residue at position 9 can be A,C or G
<220> FEATURE:
<221> NAME/KEY: misc_feature
<222> LOCATION: (10)..(10)
<223> OTHER INFORMATION: N residue at position 10 can be A, C, G or T
      and conatin 2'-o-methyl group

<400> SEQUENCE: 17 uuuuutttvn                                                           10
```